US011266705B2

(12) United States Patent
Gaudout et al.

(10) Patent No.: US 11,266,705 B2
(45) Date of Patent: Mar. 8, 2022

(54) SPECIFIC NUTRITIONAL OR THERAPEUTIC AGENT INCLUDING A MIXTURE OF GRAPE AND BLUEBERRY

(71) Applicants: ACTIV'INSIDE, Beychac et Caillau (FR); Specialites Pet Food, Elven (FR); Universite Laval, Quebec (CA); Institut National De La Recherche Scientifique (INRS), Quebec (CA)

(72) Inventors: David Gaudout, Carignan de Bordeaux (FR); Stephane Rey, Montelimar (FR); Benoit Lemaire, Libourne (FR); Julien Bensalem, Cenon (FR); Anne Lepoudere, Guer (FR); Delphine Lethuillier, Plougoumelen (FR); Marie-Eve Paradis, Quebec (CA); Stephanie Dudonne, Quebec (CA); Yves Desjardins, Quebec (CA); Frederic Calon, Quebec (CA); Alexandre Dal-Pan, Quebec (CA); Charles Ramassamy, Quebec (CA)

(73) Assignees: SPECIALITES PET FOOD, Elven (FR); ACTIV'INSIDE, Beychac et Caillau (FR); INSTITUT NATIONAL DE LA RECHERCHE SCIENTIFIQUE, Quebec (CA); UNIVERSITE LAVAL, Quebec (CA)

( * ) Notice: Subject to any disclaimer, the term of this patent is extended or adjusted under 35 U.S.C. 154(b) by 340 days.

(21) Appl. No.: 15/771,328

(22) PCT Filed: Oct. 27, 2016

(86) PCT No.: PCT/EP2016/075905
§ 371 (c)(1),
(2) Date: Apr. 27, 2018

(87) PCT Pub. No.: WO2017/072219
PCT Pub. Date: May 4, 2017

(65) Prior Publication Data
US 2018/0303891 A1    Oct. 25, 2018

(30) Foreign Application Priority Data

Oct. 27, 2015 (FR) ...................... 1560263

(51) Int. Cl.
| | | |
|---|---|---|
| A61K 36/45 | (2006.01) |
| A61K 36/87 | (2006.01) |
| A61K 31/353 | (2006.01) |
| A61K 45/06 | (2006.01) |
| A61K 9/20 | (2006.01) |
| A61K 9/48 | (2006.01) |
| A61K 31/7048 | (2006.01) |
| A61K 31/05 | (2006.01) |
| A23L 33/105 | (2016.01) |
| A61P 25/28 | (2006.01) |
| A61P 3/10 | (2006.01) |
| A61P 25/18 | (2006.01) |
| A61P 25/24 | (2006.01) |
| A61P 25/16 | (2006.01) |
| A61K 31/192 | (2006.01) |

(52) U.S. Cl.
CPC ............ *A61K 36/45* (2013.01); *A23L 33/105* (2016.08); *A61K 9/2018* (2013.01); *A61K 9/4866* (2013.01); *A61K 31/05* (2013.01); *A61K 31/192* (2013.01); *A61K 31/353* (2013.01); *A61K 31/7048* (2013.01); *A61K 36/87* (2013.01); *A61K 45/06* (2013.01); *A61P 3/10* (2018.01); *A61P 25/16* (2018.01); *A61P 25/18* (2018.01); *A61P 25/24* (2018.01); *A61P 25/28* (2018.01); *A23V 2002/00* (2013.01); *A23V 2200/322* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2006/0024385 A1 | 2/2006 | Pedersen | |
| 2008/0213401 A1 | 9/2008 | Smith | |
| 2013/0261183 A1* | 10/2013 | Bhagat | A23L 33/30 514/560 |

FOREIGN PATENT DOCUMENTS

| | | |
|---|---|---|
| MX | 2011006005 A | 12/2012 |
| WO | WO2006083666 A1 | 8/2006 |

OTHER PUBLICATIONS

Joseph J. et al., "Reversing the deleterious effects of aging on neuronal communication and behavior: beneficial properties of fruit polyphenolic compounds", American Journal of Clinical Nutrition, 2005, pp. 313S-316S, vol. 81 (Suppl 1).
Krikorian R. et al., "Blueberry supplementation improves memory in older adults", Journal of Agricultural and Food Chemistry, 2010, pp. 3996-4000, vol. 58, No. 7.

(Continued)

*Primary Examiner* — Terry A McKelvey
*Assistant Examiner* — Catheryne Chen
(74) *Attorney, Agent, or Firm* — Greer, Burns & Crain, Ltd.

(57) ABSTRACT

The invention concerns a nutritional or therapeutic agent comprising a molecule mix obtained from *Vitis vinifera* and *Vaccinium angustifolium*, comprising:
- at least 1% of catechins and epicatechins, the percentage being given by weight in relation to the total weight of the mix, preferably at least 5%,
- at least 5 ppm (parts per million in the mix) of ferulic acid, preferably at least 10 ppm.

The invention also relates to the use of this agent due to its effects on cognitive functions in particular.

12 Claims, 12 Drawing Sheets

(56) References Cited

OTHER PUBLICATIONS

Krikorian R., "Concord grape juice supplementation improves memory function in older adults with mild cognitive impairment." The British Journal of Nutrition. 2010, pp. 730-734, vol. 103, No. 5.

Rendeiro, C., "Dietary levels of pure flavonoids improve spatial memory performance and increase hippocampal brain-derived neurotrophic factor" PLOS ONE, May 2013, pp. 1-9, vol. 8, No. 5.

Van Praag H. et al. "Plant-derived flavanol (−)epicatechin enhances angiogenesis and retention of spatial memory in mice". The Journal of Neuroscience: The Official Journal of the Society for Neuroscience. May 2007, pp. 5869-5678, vol. 27, No. 22.

Cheng C. et al., "Ferulic acid provides neuroprotection against oxidative stress-related apoptosis after cerebral schemia/reperfusion injury by inhibiting ICAM-1 mRNA expression in rats". Brain Research, 2008, pp. 136-150, vol. 1209.

Sgarbossa A. et al., Ferulic Acid: A Hope for Alzheimer's Disease Therapy from Plants. Nutrients, 2015, pp. 5764-5782, vol. 7.

Yan J. et al., "Protection against β-amyloid peptide toxicity in vivo with long-term administration of ferulic acid", British Journal of Pharmacology, 2001, pp. 89-96, vol. 133.

Abraham, J. et al., "Consuming a diet supplemented with resveratrol reduced infection-related neuroinflammation and deficits in working memory in aged mice". Rejuvenation Research, 2009, pp. 445-453, vol. 12, No. 6.

Dal Pan A. et al., "Cognitive performances are selectively enhanced during chronic caloric restriction or resveratrol supplementation in a primate". PloS one, Jan. 2011, pp. 1-9, vol. 6, No. 1.

Barros D. et al. "Behavioral and genoprotective effects of Vaccinium berries intake in mice". Pharmacology, Biochemistry, and Behavior, Jun. 2006, pp. 229-234, vol. 84, No. 2.

Cho J. et al., "Antioxidant and Memory Enhancing Effects of Purple Sweet Potato Anthocyanin and Cordyceps Mushroom Extract", Archives of Pharmacal Research, 2003, pp. 821-822, vol. 26, No. 10.

Ramirez et al., "Effect of lyophilised Vaccinium berries on memory, anxiety and locomotion in adult rats. Pharmacological Research, The Official Journal of the Italian Pharmacological Society", Dec. 2005, pp. 457-462, vol. 52, No. 6.

Eubig P. et al., "Acute Renal Aailure in Dogs After the Ingestion of Grapes or Raisins: a Retrospective Evaluation of 43 Dogs", J. Vet. Intern Med, 2005, pp. 663-674, vol. 19.

Tvarijonaviciute A., "Effect of Weight Loss in Obese Dogs on Indicators of Renal Function or Disease", J. Vet. Intern. Med., 2013, pp. 31-38, vol. 27.

Garcia-Martinez J. et al., "Urinary Clusterin as a Renal Marker in Dogs", Journal of Veterinary Diagnostic Investigation, 2012, pp. 301-306, vol. 24.

Arsenault, D. et al. "PAK Inactivation Impairs Social Recognition in 3xTg-AD Mice without increasing Brain Deposition of Tau and Aβ", Neurobiology of Disease, The Journal of Neuroscience, Jun. 2013, pp. 10729-10740, vol. 33, No. 26.

Cherniack, P. "A berry thought-provoking idea: the potential role of plant polyphenols in the treatment of age-related cognitive disorders", British Journal of Nutrition, Sep. 2012, pp. 794-800, vol. 108, No. 5.

Martineau A. et al., "The consumption of a grape and blueberry polyphenol-rich mixture is safe in dogs", FASEB Journal, Apr. 2015, 1 page, vol. 29.

Dajas F. et al., "Neuroprotective Actions of Flavones and Flavonols: Mechanisms and Relationship to Flavonoid Structural Features", Central Nervous System Agents in Medicinal Chemistry, 2013, pp. 30-35, vol. 13.

\* cited by examiner

SPECIFIC NUTRITIONAL OR THERAPEUTIC AGENT INCLUDING A MIXTURE OF GRAPE AND BLUEBERRY

CROSS-REFERENCE TO RELATED APPLICATIONS

This application is a national stage application of PCT/EP2016/075905 filed Oct. 27, 2016 which claims a benefit of priority from French patent application FR 1560263 filed Oct. 27, 2015, the entire disclosures of which are herein incorporated by reference.

TECHNICAL FIELD

This invention relates to a mixture of specific polyphenols having a synergistic action particularly on the cognitive functions and executive functions in humans and animals. The invention also covers the use of this mixture to improve cognitive functions and executive functions, delay cognitive decline and prevent and combat the pathologies associated with cognitive decline in humans and animals.

BACKGROUND

It is known that old age is associated with cognitive disorders and neurodegenerative deficits such as Alzheimer's disease and Parkinson's disease. As the elderly population increases, there is a prevalence of these age-related disorders. It is therefore important to develop solutions to prevent or minimize age-related cognitive decline and delay the appearance of associated pathologies.

To this end, a prevention based on nutrition has been suggested over recent years to avoid or delay the development towards dementia and thus maintain a stable cognitive state and wellbeing in the elderly. Research dedicated to understanding the relationship between nutrition and "healthy aging" has thus intensified and among the foods studied, fruits and vegetables rich in polyphenols have been identified as capable of delaying age-related physiological and functional deficits and protecting humans or animals against associated degenerative diseases (as described for example in: Joseph J A, Shukitt-Hale B, Casadesus G "Reversing the deleterious effects of aging on neuronal communication and behavior: beneficial properties of fruit polyphenolic compounds" in the American Journal of Clinical Nutrition 2005; 81 (Suppl 1): 313S-6S). In fact, polyphenols, particularly flavonoids, are known for their ability to improve the learning process and memory and are now widely studied for their potential in the prevention of age-related cognitive decline in both animals and humans. Although the mechanisms of action of flavonoids are not clearly identified, they are known to be capable of modifying the cellular and molecular processes involved in learning and memory.

Included among the fruits containing polyphenols, studied for their effect on age-related cognitive decline, are berries in particular, and specifically blueberries, strawberries and grapes. Among the different polyphenols present in berries, those that have been specifically studied for their effect on brain functions are resveratrol and flavonoids, particularly flavanols and anthocyanins.

Blueberries are known to contain a large quantity of polyphenols and have a greater antioxidant capacity than other fruits and vegetables. Numerous studies suggest that the consumption of blueberries delays age-related functional and physiological deficits. For example, daily consumption of blueberry juice for 12 weeks improves the performance of episodic memory in the elderly (Krikorian R, Shidler M D, Nash T A, Kalt W, Vinqvist-Tymchuk M R, Shukitt-Hale B, et al. «Blueberry supplementation improves memory in older adults". Journal of Agricultural and Food Chemistry. 2010; 58(7):3996-4000).

Strawberries have a strong antioxidant and anti-inflammatory power capable of preventing age-related neurochemical and behavioral changes.

As for grapes, they are particularly rich in flavonoids (catechins, epicatechins, proanthocyanidin oligomers, procyanidin polymers and anthocyanins) known for their powerful antioxidant capacities. The nutritional properties of grapes like the source of polyphenols in wine also form the subject of numerous studies. Similar to the results obtained with blueberry juice, the consumption of grape juice for 12 weeks leads to an improvement in memory performance in the elderly (Krikorian R, Nash T A, Shidler M D, Shukitt-Hale B, Joseph J A. «Concord grape juice supplementation improves memory function in older adults with mild cognitive impairment." The British Journal of Nutrition. 2010; 103(5):730-4). Moreover, specific grape extracts (grape seed extracts, for example) are now used as a nutritional supplement due to their high concentration of polyphenols, particularly flavanols, anthocyanins and resveratrol. These extracts are suitable for nutritional supplementation because they contain a higher polyphenol concentration than fruits or juices, which facilitates the identification of their effects and the study of underlying neurobiological mechanisms. The use of berries, juices or extracts of berries to delay age-related cognitive decline and improve brain functions is therefore known. However, when humans or animals consume existing berries, juices or extracts of berries, the bioavailability of the polyphenols contained in these products is unsatisfactory and the effect on cognitive and functional functions is insufficient.

Thus, the aim of the invention is to overcome these drawbacks by proposing a product that contains polyphenols having an improved bioavailability and greater efficiency for combating cognitive decline.

SUMMARY

To this end, the invention concerns a nutritional or therapeutic agent comprising a molecule mix obtained from *Vitis vinifera* and *Vaccinium angustifolium*, comprising:
- at least 1% of catechin and/or epicatechin, the percentage being given by weight in relation to the total weight of the mix, preferably at least 5%,
- at least 5 ppm (parts per million in the mix) of ferulic acid, preferably at least 10 ppm. The agent according to the invention contains flavanols, in particular catechins and/or epicatechins, known for their effect on cognitive performance, as specifically described in Endeiro C, Vauzour D, Rattray M, Waffo-Teguo P, Merillon J M, Butler L T, et al. "*Dietary levels of pure flavonoids improve spatial memory performance and increase hippocampal brain-derived neurotrophic factor*" PloS one. 2013; 8(5):e63535, as well as Van Praag H, Lucero M J, Yeo G W, Stecker K, Heivand N, Zhao C, et al. "*Plant-derived flavanol (−)epicatechin enhances angiogenesis and retention of spatial memory in mice*". The Journal of Neuroscience: the official journal of the Society for Neuroscience. 2007; 27(22):5869-78.

Similarly, ferulic acid is known for its effects on the nervous system, particularly to protect neuronal cells from cell death caused by cerebral ischemia as described specifically in Cheng C Y S, S. Y.; Tang, N.Y.; Ho, T. Y.; Chiang, S. Y.; Hsieh, C. L. "*Ferulic acid provides neuroprotection against oxidative stress-related apoptosis after cerebral ischemia/reperfusion injury by inhibiting ICAM-1 mRNA expression in rats*". Brain Res. 2008; 1209:136-50. Moreover, its antioxidant activity has been tested in Alzheimer's disease (Sgarbossa A, Giacomazza D, Di Carlo M. "*Ferulic Acid: A Hope for Alzheimer's Disease Therapy from Plants. Nutrients*". 2015; 7(7):5764-82) and its long-term administration seems to protect against memory and learning deficits (Yan J J C, J. Y.; Kim, H. S.; Kim, K. L.; Jung, J. S.; Huh, S. O.; Suh, H. W.; Kim, Y. H.; Song, D. K. "*Protection against β-amyloid peptide toxicity in vivo with long-term administration of ferulic acid*". Br J Pharmacol. 2001; 133:89-96).

This effect is further increased when the agent also comprises:
- at least 200 ppm of resveratrol, and/or
- at least 50 ppm of quercetin and/or quercetin glycosides, and/or
- at least 500 ppm of anthocyanidins.

These molecules are also known for their effect on cognitive functions.

Resveratrol also has numerous beneficial activities for humans or animals, including an improvement in working memory, learning and spatial memory and spontaneous motor activity (Abraham J, Johnson R W. «*Consuming a diet supplemented with resveratrol reduced infection-related neuroinflammation and deficits in working memory in aged mice*". Rejuvenation research. 2009; 12(6):445-53; Dal-Pan A, Pifferi F, Marchal J, Picq J L, Aujard F. "*Cognitive performances are selectively enhanced during chronic caloric restriction or resveratrol supplementation in a primate*". PloS one. 2011; 6(1):e16581. Resveratrol is particularly known for possibly being present in grapes, but is not present in all grape extracts. In fact, resveratrol is a phytoalexin that develops basically on the grape skin in a very variable manner and its presence in extracts, as with other molecules, is also dependent on the extraction method used.

Quercetin also has a significant neuroprotective action (Dajas F, Andres A C, Florencia A, Carolina E, Felicia R M. "*Neuroprotective actions of flavones and flavonols: mechanisms and relationship to flavonoid structural features. Central nervous system agents in medicinal chemistry.*" 2013; 13(1):30-5) and it is also known that the consumption of foods rich in anthocyanidins prevents memory deficiencies and improves cognitive performance (Barros D, Amaral O B, Izquierdo I, Geracitano L, do Carmo Bassols Raseira M, Henriques A T, et al. "*Behavioral and genoprotective effects of Vaccinium berries intake in mice*". Pharmacology, Biochemistry, and Behavior. 2006; 84(2):229-34; Cho J, Kang J S, Long P H, Jing J, Back Y, Chung K S. "*Antioxidant and memory enhancing effects of purple sweet potato anthocyanin and cordyceps mushroom extract. Archives of Pharmacal Research*". 2003; 26(10):821-5; Ramirez M R, Izquierdo I, do Carmo Bassols Raseira M, Zuanazzi J A, Barros D, Henriques A T. "*Effect of lyophilised Vaccinium berries on memory, anxiety and locomotion in adult rats. Pharmacological Research: the official journal of the Italian Pharmacological Society*". 2005; 52(6):457-62).

Surprisingly, the combination and specific quantity of polyphenols present in the agent has a synergistic effect and increases the bioavailability of the polyphenols when they are administered to humans or animals in comparison to the bioavailability of these same polyphenols when they are administered in isolation or via existing berry extracts or when consuming grapes or blueberries or at different concentrations in existing products. The molecules of the mixture and consequently the agent according to the invention have in particular an antioxidant synergistic effect and/or an effect on the improvement of cognitive and/or executive functions in humans or animals.

The agent according to the invention is therefore particularly useful notably as a drug for humans or animals, and specifically to prevent and/or combat pathologies associated with cognitive decline.

Similarly, the invention also concerns the use of such an agent for non-therapeutic nutritional applications in healthy humans or animals, particularly to improve cognitive and/or executive functions.

BRIEF DESCRIPTION OF THE DRAWINGS

The invention is now described in detail with reference to the accompanying figures, in which.

DETAILED DESCRIPTION

Figure 1:
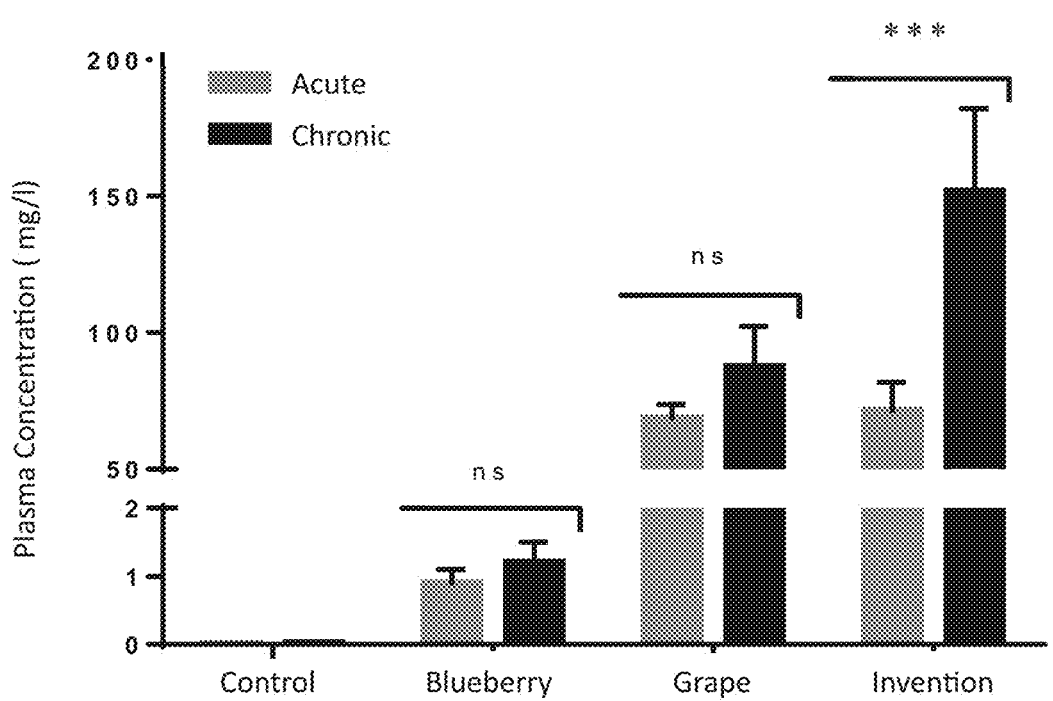
FIG. 1 shows the differences in bioavailability of polyphenols in mouse plasma, between an acute administration and a chronic administration of an extract of *Vitis vinifera*, an extract of *Vaccinium angustifolium* or of an agent according to the invention.

The subject matter of the invention therefore concerns a nutritional or therapeutic agent comprising at least one molecule mix obtained from *Vitus vinifera* and *Vaccinium angustifolium*, said mix comprising:

at least 1% of catechin and/or epicatechin, the percentage being given by weight in relation to the total weight of the mix, preferably at least 5%, even more preferably between 5% and 50%, specifically between 7% and 35%, at least 5 ppm (parts per million in the mix) of ferulic acid, preferably at least 10 ppm, even more preferably between 5 ppm and 300 ppm, specifically between 10 ppm and 100 ppm.

Preferably, in addition to the at least 1% of catechin and/or epicatechin, and at least 5 ppm of ferulic acid, the molecule mix according to the invention also comprises:

at least 200 ppm of resveratrol, preferably at least 300 ppm, even more preferably at least 400 ppm, even more preferably between 300 ppm and 6000 ppm, specifically between 400 and 6000 ppm, and/or at least 50 ppm of quercetin and/or quercetin glycosides, preferably at least 70 ppm of quercetin and/or glycoside, specifically between 50 ppm and 10000 ppm, and/or at least 500 ppm of anthocyanidins, preferably at least 600 ppm, even more preferably at least 700 ppm, even more preferably between 600 ppm and 5000 ppm.

Preferably, malvidin 3-glucoside is the preponderant anthocyanidin. It is preferably present at a concentration of at least 300 ppm in the mix.

"Nutritional agent" in the sense of the invention means a food ingredient with a nutritional purpose used alone or associated with other food ingredients or additives in food formulas including food supplements intended for humans or animals.

"Therapeutic agent" in the sense of the invention means an active ingredient used for therapeutic purposes alone or associated with other active substances or not in drug formulas including phytotherapy, intended for humans or animals.

"Anthocyanidin" in the sense of the invention means all anthocyanins or anthocyanosides, in aglycone or glycosylated form (i.e. bearing sugars). Thus, in the present application and in the sense of the present invention, the terms "anthocyanidin", "anthocyanins" and "anthocyanosides" are equivalent.

"At least X % of catechins and/or epicatechins" means either at least X % of catechins if there are no epicatechins in the mix, or at least X % of epicatechins if there are no catechins in the mix, or at least X % of the mix of catechins and epicatechins if both catechins and epicatechins are present in the mix at the same time. Preferably, this means at least X % of the mix of catechins and epicatechins.

"Ppm" means parts per million (mg/kg) in the mix. Unless stated otherwise, ppm refers to a weight in relation to the total weight of the mix.

According to a first embodiment, the molecule mix is a mixture formed by an extract of *Vitis vinifera* and an extract of *Vaccinium angustifolium*.

According to a second embodiment, the molecule mix is a mixture formed by an extract obtained from a mixture of *Vitis vinifera* and *Vaccinium angustifolium*.

According to a third embodiment, the molecule mix is a mixture formed by:

an extract of *Vitis vinifera* and/or an extract of *Vaccinium angustifolium*, and an extract obtained from a mixture of *Vitis vinifera* and *Vaccinium angustifolium*.

"Extract of *Vitis vinifera*" in the sense of the invention means at least one molecule preferably a collection of molecules, obtained from *Vitis vinifera*. The raw material can be the leaves and/or fruits and/or seeds and/or wood, preferably the raw material is the above-ground part of the plant, i.e. the leaves, fruits, pellicle (i.e. the skin), seeds and wood, even more preferably the skin (pellicle) and seeds. The association of the skin, which can be rich in resveratrol, and the seeds, which can be rich in flavanol monomers, in procyanidin oligomers and in proanthocyanidins, can be particularly advantageous for the invention.

Preferably, the extract of *Vitis vinifera* is an extract having a flavanol polymer content of less than 0.5% by weight of the total weight of the polyphenols of the extract, even more preferably a content of less than 0.1%. "Flavanol polymer" means a flavanol having a degree of polymerisation of more than 10. According to the invention, the flavanol polymers have very little bioavailability, unlike flavanol monomers that are very quickly absorbed into the small intestine then metabolized into methylated, sulfated and glucuronidated derivatives.

This low presence of polymers is a quality criterion of grape extracts used in particular due to their efficacy and bioavailability.

"Extract of *Vaccinium angustifolium*" in the sense of the invention means at least one molecule, preferably a combination of molecules, obtained from *Vaccinium angustifolium*. The raw material can be the leaves and/or fruits, preferably the raw material is the combination of the leaves and fruits of the plant.

Extract obtained from a mixture of *Vitis vinifera* and *Vaccinium angustifolium* means a combination of molecules obtained from a mixture of *Vitis vinifera* and *Vaccinium angustifolium*. The raw material of *Vitis vinifera* can be the leaves and/or the fruits and/or the seeds and/or the wood, preferably the raw material of *Vitis vinifera* is the above-ground part of the plant, i.e. the combination of leaves, fruit, skin (pellicle), seeds and wood, more preferably the skin (pellicle) and seeds. The raw material of *Vaccinium angustifolium* can be the leaves and/or fruits, preferably the raw material of *Vaccinium angustifolium* is the combination of the leaves and fruits of the plant.

The extract according to the invention can be obtained by any method allowing a mix to be obtained that comprises:

at least 1% of catechin and/or epicatechin by weight in relation to the total weight of the mix, preferably at least 5%, even more preferably between 5% and 50%, specifically between 7% and 35%, at least 5 ppm of ferulic acid, preferably at least 10 ppm, even more preferably between 5 ppm and 300 ppm, specifically between 10 ppm and 100 ppm, optionally, at least 200 ppm of resveratrol, preferably at least 300 ppm, even more preferably at least 400 ppm, even more preferably between 300 ppm and 6000 ppm, specifically between 400 and 6000 ppm, optionally, at least 50 ppm, of quercetin and/or quercetin glycosides, preferably at least 70 ppm, of quercetin and/or glycoside, specifically between 50 ppm and 10000 ppm, optionally, at least 500 ppm of anthocyanidins, preferably at least 600 ppm, even more preferably at least 700 ppm, even more preferably between 600 ppm and 5000 ppm.

Preferably malvidin 3-glucoside is the preponderant anthocyanidin with a concentration of at least 300 ppm. Preferably, the anthocyanidins comprise at least 20%, more preferably at least 25% of malvidin 3-glucoside (percentage by weight).

A particularly appropriate method is a method comprising the following steps:

obtaining an extract of *Vitis vinifera*:
  water and/or ethanol extraction of *Vitis vinifera*, preferably from the combination of leaves, fruits, pellicle, seeds and wood of *Vitis vinifera*. The quantity of solvent (30% v/v to 96% v/v) used is between 2 and 10 times the mass of material used. The duration of the extraction can be between 30 minutes and 24 hours and the extraction temperature between 20° C. and 80° C. The raw materials used can be in dry, fresh or whole frozen or ground form;
  separation of the solution of water and/or ethanol from the solid matter, for example by centrifugal decantation or by pressing and filtration;
  evaporation of the ethanol under vacuum evaporation at a temperature preferably below 60° C. and at a pressure below 100 mbars;
  membrane separation of the extract previously desolvented so as preferably to select the proanthocyanidic monomers and oligomers (having a degree of polymerization of between 2 and 10 inclusive) and eliminate the flavanol polymers (>decamers), in order to obtain an extract characterized by a flavanol polymer content of less than 0.5% and more preferably less than 0.1% by weight in relation to the total weight of the polyphenols of the extract. This step can be performed with the aid of a filtration membrane having a cut-off threshold of less than 15000 daltons and more preferably less than 3000 daltons;
obtaining an extract of *Vaccinium angustifolium*:
  water and/or ethanol extraction of *Vaccinium angustifolium*, preferably from the leaves and fruits of *Vaccinium angustifolium*. The quantity of solvent (30% v/v to 96% v/v) used is between 2 and 10 times the mass of material used. The duration of the extraction can be between 30 minutes and 24 hours and the extraction temperature between 20° C. and 80° C. The raw materials used can be in dry, fresh or frozen form;
  separation of the solution of water and/or ethanol from the solid matter by centrifugal decantation or by pressing and filtration;
  evaporation of the ethanol under vacuum evaporation at a temperature preferably below 60° C. and at a pressure below 100 mbars;
drying the extracts by spray drying, in a vacuum oven or by freeze drying with or without a support such as a maltodextrin;
mixing the extract of *Vitis vinifera* and *Vaccinium angustifolium* before or after the drying step.

According to a variation, the method consists in implementing the following steps:
  mixing *Vitis vinifera* and *Vaccinium angustifolium*, water and/or ethanol extraction of *Vaccinium angustifolium*, preferably from the combination of the leaves and fruits of *Vaccinium angustifolium*. The quantity of solvent (30% v/v to 96% v/v) used is between 2 and 10 times the mass of material used. The duration of the extraction can be between 30 minutes and 24 hours and the extraction temperature between 20° C. and 80° C. The raw materials used can be in dry, fresh or frozen form;
  separation of the solution of water and/or ethanol from the solid pomace by centrifugal decantation or by pressing and filtration;
  evaporation of the ethanol under vacuum evaporation at a temperature preferably below 60° C. and at a pressure below 100 mbars;
  drying the extract by spraying or sublimation with or without a support such as maltodextrin.

Whatever the variation of the method, before the drying step, the method can comprise the following steps:
  loading onto a resin of solutions of mixed or unmixed extracts,
  rinsing the resin with water,
  applying an eluent solution of water/ethanol onto the resin,
  recovering the purified eluate,
  evaporating the ethanol from said eluate,
  concentrating said eluate,
  drying said purified aqueous extract.

The nutritional or therapeutic agent according to the invention can consist exclusively of a mixture of molecules, i.e. extracts, or comprise other constituents. Preferably, in addition to the mixture of molecules, the nutritional or therapeutic agent according to the invention contains other constituents, in particular excipients or coating agents, such as maltodextrin, microcrystalline cellulose, cyclodextrins, starch and soluble or insoluble fibers.

The agent can be in any form suitable for a nutritional or therapeutic application, preferably in powder form.

The agent according to the invention can be incorporated in a composition, in particular in a nutritional or therapeutic (drug) composition if in a form chosen from tablets, capsules, gel capsules, powders, solutions, microcapsules, suspensions, emulsions, food supplements, drinks and food for humans or animals.

It may be a non-therapeutic nutritional composition intended for humans such as, for example, food supplements, bars, dairy products, powders to be swallowed or rehydrated, gels, jams, sweets, carbonated and non-carbonated beverages, dry beverages to be rehydrated and compotes.

It may also be a drug intended for humans such as, for example, tablets or capsules.

It may also be a nutritional or therapeutic composition intended for animals. An "animal" means any animal capable of receiving a nutritional or therapeutic agent according to the invention, for example but in a non-limiting manner a pet, a fowl, a pig, a ruminant, a goat or even a mouse. Preferably, the animal is a pet, such as a cat or dog. More preferably, the animal is a dog.

It may also be a non-therapeutic nutritional composition intended for an animal such as, for example, dry foods, such as kibbles (extruded, co-extruded or freeze dried), treats, snacks, wet or semi-wet foods such as pieces in sauce, chunks in jelly, beverages, or even food supplements. Preferably, the agent is incorporated in dry foods such as kibbles.

Lastly, it can be a drug intended for animals, or a veterinary product, such as, for example, tablets, capsules, sprays and liquids administered dropwise.

Advantageously, the agent intended for animals can be incorporated into a composition, in particular into a nutritional or therapeutic composition, as an inclusion, namely by adding it to the mass of the composition for example by impregnation or mixing, or as a coating, namely by applying it to the surface of the composition, by spraying or by dusting, for example by mixing it beforehand with one or more ingredients such as at least one palatability enhancer.

The nutritional or therapeutic agent can be used in particular to act on the cognitive and executive functions in a healthy individual or animal but also in sick subjects.

Cognitive decline is characterized by an age-related reduction in the cognitive and executive functions, particularly concentration, work, long-term memory, ability to reason, judge, solve problems and speed of processing information. These deficiencies can lead to a reduction in self-esteem and quality of life. Age-related cognitive decline is the term used to described the non-pathological form of the deterioration of memory and cognitive functions resulting from the aging process within normal limits, taking into account a person's age. This is a complex process, with the first signs emerging in humans between 35 and 65 years, with no specific neurodegenerative lesions. Gradual cognitive decline can be manifested by the appearance of minor cognitive problems that affect 15 to 20% of the population aged 65 or over, but that represent an unstable condition. However, certain pathological forms can arise in addition to this "normal" cognitive decline. Among these pathologies, Alzheimer's disease is the most common cause of dementia, affecting over 24 million people worldwide. It is irreversible within our current state of knowledge, the only treatments available being purely symptomatic. In animals, these pathologies can manifest themselves in a very similar manner.

In dogs, for example, cognitive dysfunction syndrome (or CDS) is a widespread pathology characterized by spatio-temporal disorientation, a loss of elementary learning that often leads to uncleanliness, a change in sleep/wake cycles and a change in social interactions.

The agent according to the invention is capable of improving the cognitive and executive functions in humans or animals. The association of two raw materials and the specificity of the extracts according to the invention comprising polyphenols combined in specific quantities, produces a synergistic effect in comparison to polyphenols taken alone or to existing extracts containing polyphenols in different proportions and quantities. The synergy focuses on the antioxidant effect and/or on the improvement of the cognitive and/or executive functions in humans or animals.

The polyphenols present in the agent according to the invention, when administered to humans or animals, also have an improved bioavailability compared to polyphenols taken alone or to existing extracts containing these polyphenols in different proportions and quantities. The agent according to the invention used in humans or animals thus allows the bioavailability of the polyphenols contained in said agent to be improved.

The agent according to the invention can be used as a drug for humans or animals. In particular, the invention relates to the use of the therapeutic or nutritional agent in the treatment or prevention in humans or animals of Alzheimer's disease and/or Parkinson's disease and/or Huntington's disease and/or pathological cognitive decline and/or dementia and/or depression and/or diabetes and/or schizophrenia and/or mental retardation and/or disorders relating to the post-menopausal condition in women and/or cognitive dysfunction syndrome (CDS).

The agent according to the invention can also be used in healthy humans or animals, for a non-therapeutic use, to improve cognitive functions and/or executive functions, and/or to limit age-related non-pathological cognitive decline, preferably in a nutritional composition or a food supplement. It can in particular be used in healthy humans or animals to improve memory and/or attention and/or concentration and/or alertness and/or learning and/or intelligence and/or language and/or mood and/or stress and/or anxiety and/or outlook and or sleep.

According to a particular embodiment of the invention, the human or animal is elderly. Preferably the elderly human or animal is a human or animal who has completed at least 50% of the average lifespan for his/its species.

Preferably, the therapeutic or nutritional agent is used as a dose, a quantity that provides the sick human or animal for therapeutic uses or a healthy human or animal for non-therapeutic uses:
  at least 100 µg per kg of body weight of catechin and/or epicatechin,
  preferably at least 0.05 µg per kg of body weight of ferulic acid,
  at least 10 µg per kg of body weight of resveratrol,
  at least 0.2 µg per kg of body weight of quercetin and/or quercetin glycosides, and
  at least 1 µg per kg of body weight of anthocyanidins.

The invention is described here through examples and test results proving the antioxidant synergistic effect and the effect on cognitive and executive functions, and the improvement of bioavailability of the therapeutic or nutritional agent covered by the present application.

EXAMPLES

Example 1: Therapeutic or Nutritional Agent According to the Invention

This first example of a mixture according to the invention is obtained by adopting the method described below.
The raw materials used are:
  the skin and seeds (pips) of the fruits of *Vitis vinifera*, by-products of the wine industry,
  frozen *Vaccinium angustifolium* berries.

400 g of frozen *Vaccinium angustifolium* berries are crushed and mixed with a solution of 2000 ml of 80% (v/v) ethanol with a content of 0.1% by weight of HCl. The mixture is kept at ambient temperature (20° C.) for 24 hours. The ethanolic solution is then separated from the pulp by filtration, and under vacuum-concentrated with a rotary evaporator to 20% of dry matter. Part of this extract is preserved for testing, the other part is kept to be mixed with the extract of *Vitis vinifera*.

500 g of pellicle and seeds of *Vitis vinifera* are mixed with 2500 ml of 80% (v/v) ethanol with a 0.1% content by weight of HCl at 40° C. for 5 hours. The ethanolic solution is then separated from the pulp by filtration. The ethanol is then under vacuum removed with a rotary evaporator at a temperature of 50° C. at 60 mbars. The aqueous solution is then diluted to obtain 5% dry matter and filtered through a 5000-dalton membrane. The permeate obtained is then loaded onto a resin column (C18) at 1 BV/hour. The resin is then flushed for a first time with 3 BV of distilled water at 2 BV/hour and then eluted with 5 BV of an 80% (v/v) ethanolic solution at 1 BV/hour. Part of the extracted solution is kept for testing and is characterized (Table 1a).

The polyphenols presented in this table were measured by ultra performance liquid chromatography with a fluorescence detector.

TABLE 1a

Flavanol content of the extract of *Vitis vinifera*
Flavanol monomer and proanthocyanidin content
(dry weight %-eq. Epicatechins)
(measured by LC with a fluorescence detector)

| | |
|---|---|
| Monomers | 35.27% ± 1.67 |
| Dimers | 22.92% ± 1.31 |
| Trimers | 8.93% ± 0.46 |
| Tetramers | 2.95% ± 0.14 |
| Pentamers | 1.09% ± 0.07 |
| Hexamers | 0.63% ± 0.14 |

TABLE 1a-continued

Flavanol content of the extract of *Vitis vinifera*
Flavanol monomer and proanthocyanidin content
(dry weight %-eq. Epicatechins)
(measured by LC with a fluorescence detector)

| | |
|---|---|
| Heptamers | 0.15% ± 0.05 |
| Octamers | Not Detected |
| Nonamers | Not Detected |
| Decamers | Not Detected |
| Polymers (Degree of polymerization >10) | Not Detected |

The other part is then mixed with the extract of *Vaccinium angustifolium* to form the mix according to the invention and a maltodextin is added to the mix until a solution is obtained that has a dry matter content of 30%.

The solution is then spray-dried at an inlet temperature of 160° C.

The product obtained is a purple powder containing the polyphenols presented in Table 1b.

The polyphenols presented in this Table were measured by ultra-performance liquid chromatography tandem mass spectrometry (UPLC-MS/MS).

TABLE 1b

Polyphenol content of the agent according to
the invention of Example 1

| | Mixture according to the invention | 500 mg of mixture/kg of mouse body weight | Equivalent in mg/kg (humans according to the FDA) |
|---|---|---|---|
| Catechin and epicatechin | 25.7% | 128.5 mg/kg of body weight | 10.4 mg/kg of body weight |
| Anthocyanidins (of which malvidin 3-glucoside) | 0.436% (1310 ppm) | 2.18 mg/kg of body weight | 177 µg/kg of body weight |
| Quercetin and quercetin glycosides | 0.864% | 4.32 mg/kg of body weight | 35 µg/kg of body weight |
| Ferulic acid | 0.0094% | 47 µg/kg of body weight | 3.82 µg/kg of body weight |
| Resveratrol | 0.0437% | 218 µg/kg of body weight | 17.7 µg/kg of body weight |

Example 2: Therapeutic or Nutritional Agent According to the Invention

This second example of a mixture according to the invention is obtained by adopting the method described below.

The raw materials used are:

the seeds and skin of *Vitis vinifera*

*Vaccinium angustifolium* berries.

1000 g of frozen pomace of *Vaccinium angustifolium* are crushed and mixed with a solution of 5000 ml of 60% (v/v) ethanol with a content of 0.1% by weight of HCl. The mixture is kept at ambient temperature (20° C.) for 24 hours. The ethanolic solution is then separated from the pulp by filtration, and under vacuum-concentrated with a rotary evaporator to 20% of dry matter.

400 g of skin and seeds of *Vitis vinifera* are selected and mixed with 1500 ml of 80% (v/v) ethanol at 60° C. for 5 hours. The ethanolic solution is then separated from the pulp by filtration. The ethanol is then under vacuum-removed with a rotary evaporator at a temperature of 50° C. at 60 mbars. The aqueous solution is then diluted to give 5% dry matter and filtered through a 5000-dalton membrane. The permeate obtained is then loaded onto a resin column (C18) at 1 BV/hour. The resin is then flushed for a first time with 3 BV of distilled water at 2 BV/hour and then eluted with 5 BV of an 80% (v/v) ethanolic solution at 1 BV/hour. Part of the extracted solution is kept for testing and characterization (Table 2a).

TABLE 2a

Flavanol content of the extract of *Vitis vinifera*
Flavanol monomer and proanthocyanidin content
(dry weight %-eq. Epicatechins) (measured by
LC with a fluorescence detector)

| | |
|---|---|
| Monomers | 9.4% ± 0.8 |
| Dimers | 4.0% ± 0.3 |
| Trimers | 0.81% ± 0.1 |
| Tetramers | 0.24% ± 0.1 |
| Pentamers | Not Detected |
| Hexamers | Not Detected |
| Heptamers | Not Detected |
| Octamers | Not Detected |
| Nonamers | Not Detected |
| Decamers | Not Detected |
| Polymers (Degree of polymerization >10) | Not Detected |

The product obtained is a purple powder containing the polyphenols presented in Table 2b. The polyphenols presented in this Table were measured by ultra-performance liquid chromatography tandem mass spectrometry (UPLC-MS/MS).

TABLE 2b

Polyphenol content of the agent according to the invention of Example 2

| | Mixture according to the invention | 4 mg of mixture/ kg of mouse body weight | Equivalent in mg/kg (humans according to the FDA) |
|---|---|---|---|
| Catechin and epicatechin | 9.4% | 376 µg/kg of body weight | 124 µg/kg of body weight |
| Anthocyanidins (of which malvidin 3-glucoside) | 700 ppm (328 ppm) | 2.8 µg/kg of body weight | 1.6 µg/kg of body weight |
| Quercetin and quercetin glycosides | 77 ppm | 0.37 µg/kg of body weight | 0.21 µg/kg of body weight |
| Ferulic acid | 20 ppm | 0.08 µg/kg of body weight | 0.044 µg/kg of body weight |

TABLE 2b-continued

Polyphenol content of the agent according to the invention of Example 2

|  | Mixture according to the invention | 4 mg of mixture/ kg of mouse body weight | Equivalent in mg/kg (humans according to the FDA) |
| --- | --- | --- | --- |
| Resveratrol | 5327 ppm | 21 µg/kg of body weight | 12 µg/kg of body weight |

Example 3: Therapeutic or Nutritional Agent According to the Invention 19.980 kg of the agent of Example 1 is mixed with 0.020 kg of colloidal silica. The composition is obtained by mixing the constituents under conventional conditions known to a person skilled in the art. The agent is placed in a PET bag, which is then placed in a box.

Example 4: Nutritional Composition Intended for Humans

Example 4 is a 400 mg capsule formed by:
Therapeutic agent of Example 1: 300 mg
Vitamin C: 80 mg
Maltodextrin: 20 mg The composition is obtained by mixing the constituents under conventional conditions known to a person skilled in the art, and put into a capsule also according to conventional conditions. The recommended dose is 1 to 2 capsules per day.

Example 5: Drug Intended for Humans

Example 5 is a 3000 mg tablet, formed by:
Therapeutic agent of Example 1: 1500 mg
Sorbitol: 1400 mg
Red fruit flavoring: 47 mg
Magnesium stearate: 30 mg
E133 Lake Brilliant Blue FCF dye: 20 mg
Acesulfame K (E950): 1.5 mg
Sodium saccharin (E954): 1.5 mg The composition is obtained by mixing the constituents under conventional conditions known to a person skilled in the art.

The recommended dose is 1 to 2 tablets per day.

Example 6: Nutritional Composition for Animals

The agent according to the invention of Example 2 was added to a dry extruded kibble for dogs according to AFCO standards and comprising animal meal, fat, fibers, cereals, preserving agents and antioxidants.

The addition of the agent to the kibble was performed according to several embodiments, specifically by coating and inclusion.

Coating tests were carried out by adding the agent according to the invention to a liquid palatability enhancer D'Tech Poultry (SPF, Elven, France). A first layer of poultry fat (6% in relation to the weight of the kibble) was added as a coating on the kibble, followed by a layer of mixture between the palatability enhancer (1%, 2% or 3%, the % being relative to the weight of the kibble) and the agent according to the invention (0.02%, 0.04% or 0.1%, the % being relative to the weight of the kibble).

Inclusion tests were performed by adding the agent according to the invention (0.02%, 0.04% or 0.1%, the % being relative to the weight of the kibble) to the raw material (also called premix) before extrusion.

Example 7: Veterinary Product

Gelatin capsules were prepared according to a standard procedure, by adding an agent according to the invention of Example 2 and a maltodextrin (Control: Glucidex12 Batch #421A323532, Roquette, Lestrem Cedex, France).

Evaluation of the Efficacy and Bioavailability of the Agent According to the Invention Test 1: Effect on Bioavailability in Mice The purpose of this test is to compare the bioavailability of the polyphenols contained in the therapeutic or nutritional agent according to the invention (mixture of Example 1) with the bioavailability of the polyphenols contained in an extract of *Vitis vinifera* and those contained in an extract of *Vaccinium angustifolium* (those described in Example 1), after an acute oral (1 day) and chronic (15 days) administration to mice.

Seventy-two 4-month-old male and female mice were divided into two groups to perform the acute study and chronic study separately. In each group, three sub-groups of 10 were created, each sub-group receiving a different treatment: extract of *Vitis vinifera*, extract of *Vaccinium angustifolium* and mixture of Example 1, and a fourth sub-group of 6 mice were treated with water (control group). The treatments were administered orally by gavage. The mixture was administered at a dose of 500 mg/kg of body weight, and the extract of *Vitis vinifera* and the extract of *Vaccinium angustifolium* were administered at a dose equivalent to their quantity in the mixture dose.

Acute study: blood samples were taken from each group, before gavage then 30 minutes after gavage for each respective treatment. The animals were then sacrificed and blood samples were again taken.

Chronic study: blood samples were collected before supplementation (Day 0). The animals then received their respective treatment each day, for 15 days. The last day of the study (Day 15), 30 minutes after gavage, the animals were sacrificed and blood samples were collected. The excrement was collected for each mouse before and during the supplementation period (Day 0 and Days 1 to 15 respectively). The phenolic metabolites were extracted from samples of plasma and dry excrement by solid-phase micro extraction (µSPE) and characterized by UHPLC-MS/MS (ultra high-performance liquid chromatography). The plasma concentrations of the phenolic metabolites after acute and chronic administration of the different treatments were compared by using Welch's statistical test (correction of unequal variance) when the data were presumed to be normally distributed or, when this was not the case, by using the Mann-Whitney test, with GraphPad Prism 6.05 software. Similarly, the effects of the treatments on the concentrations of circulating phenolic metabolites and the concentrations accumulated in the excrement were analyzed for pairwise comparison using Welch's statistical test if the data were normal and the Mann-Whitney test if they were not.

Multiple comparisons were made using a variance analysis (ANOVA) or the non-parametric Kruskal-Wallis test, a test based on data following a normal or abnormal distribution. The differences were considered to be significant at $p<0.05$.

The ascending hierarchical classification (AHC) of the phenolic metabolites detected in the plasma and excrement of mice was achieved using MetaboAnalyst 3.0.

Figure 2:
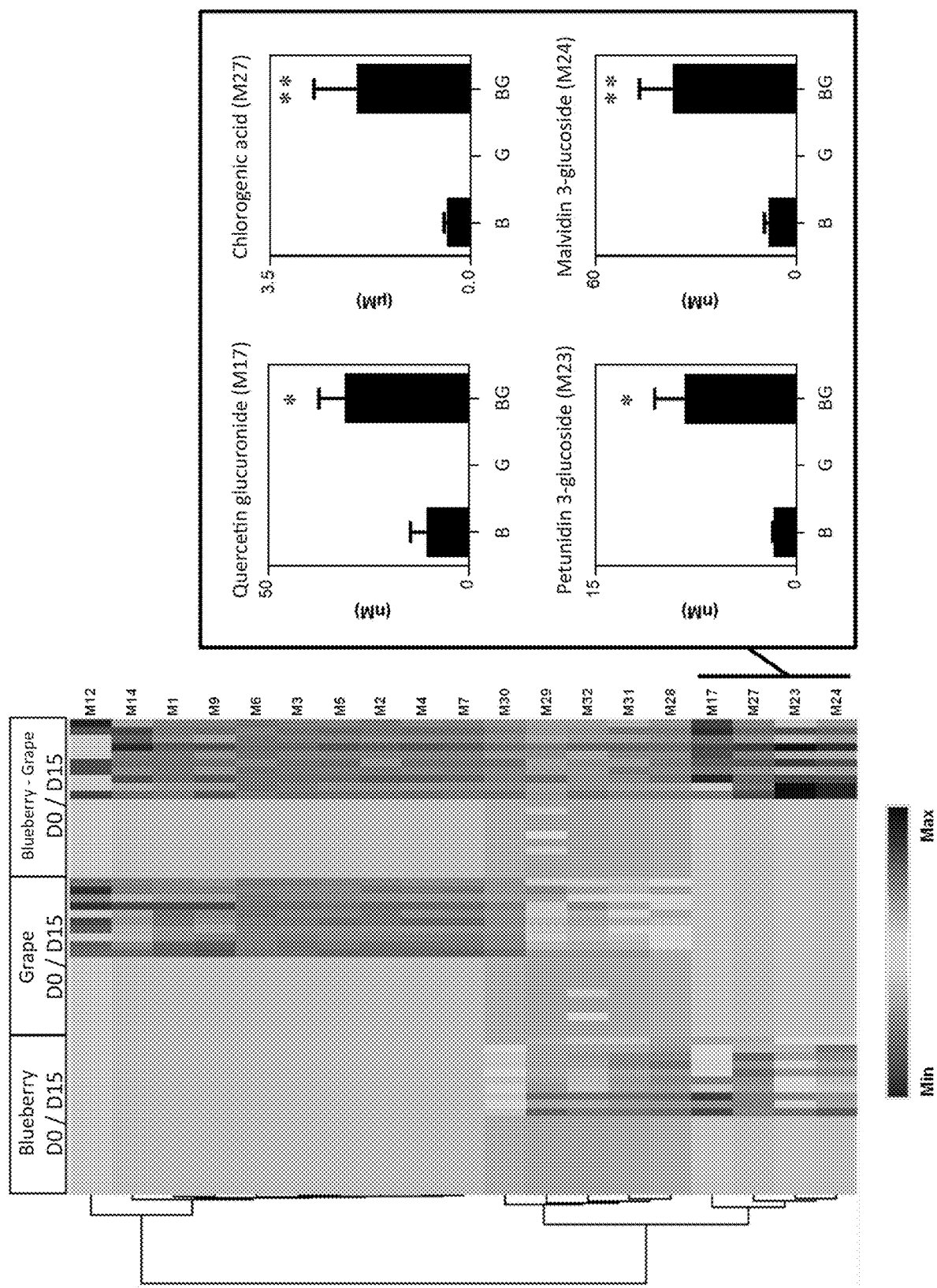
FIG. 2 shows the ascending hierarchical classification (AHC) of the phenolic metabolites found in mouse plasma before and after treatment by chronic ingestion of an extract of *Vitis vinifera*, an extract of *Vaccinium angustifolium* or of an agent according to the invention.
Figure 3:
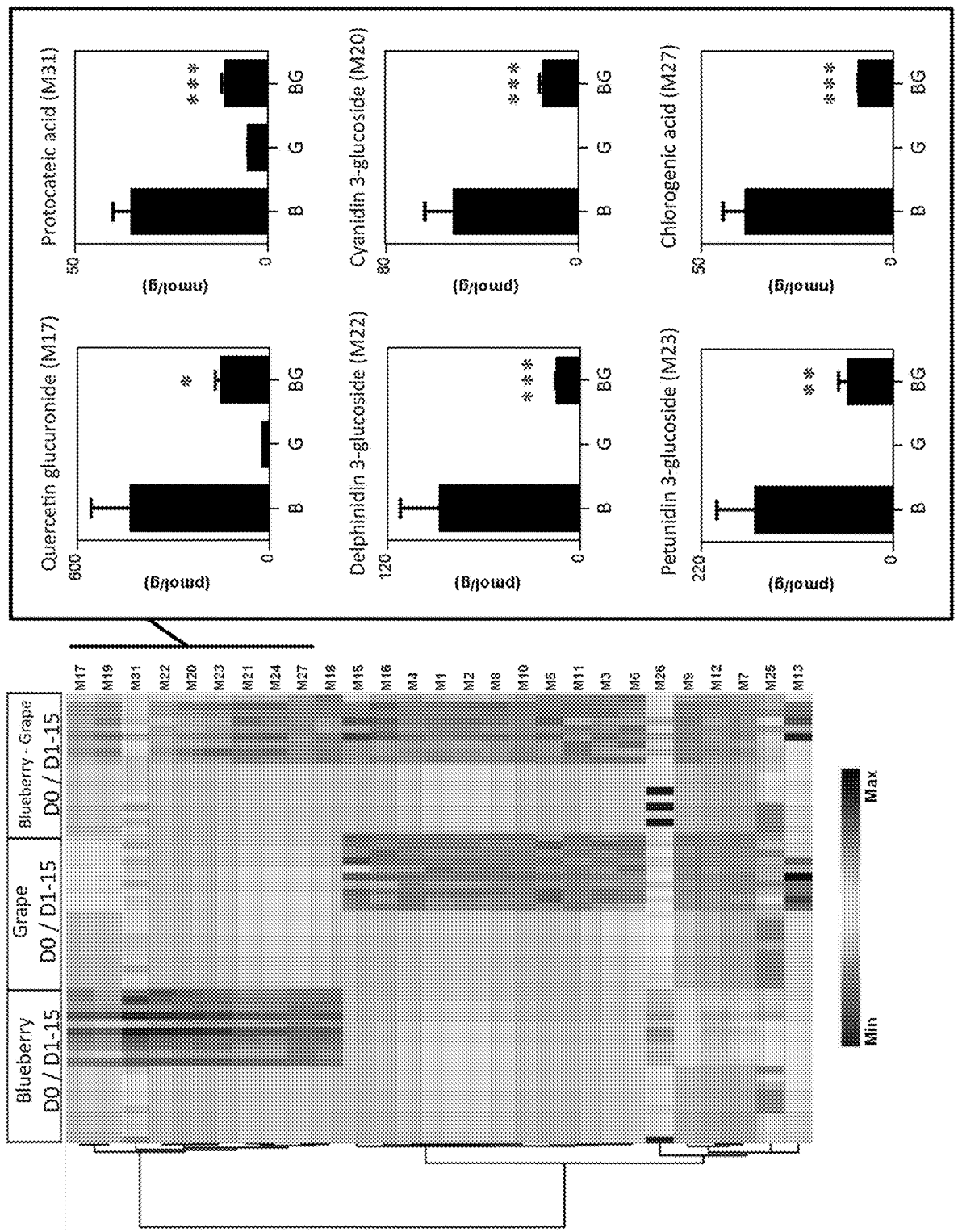
FIG. 3 shows the ascending hierarchical classification (AHC) of the phenolic metabolites found in mouse excrement before and after treatment by chronic ingestion of an extract of *Vitis vinifera*, of an extract of *Vaccinium angustifolium* or of an agent according to the invention.
Figure 4A:
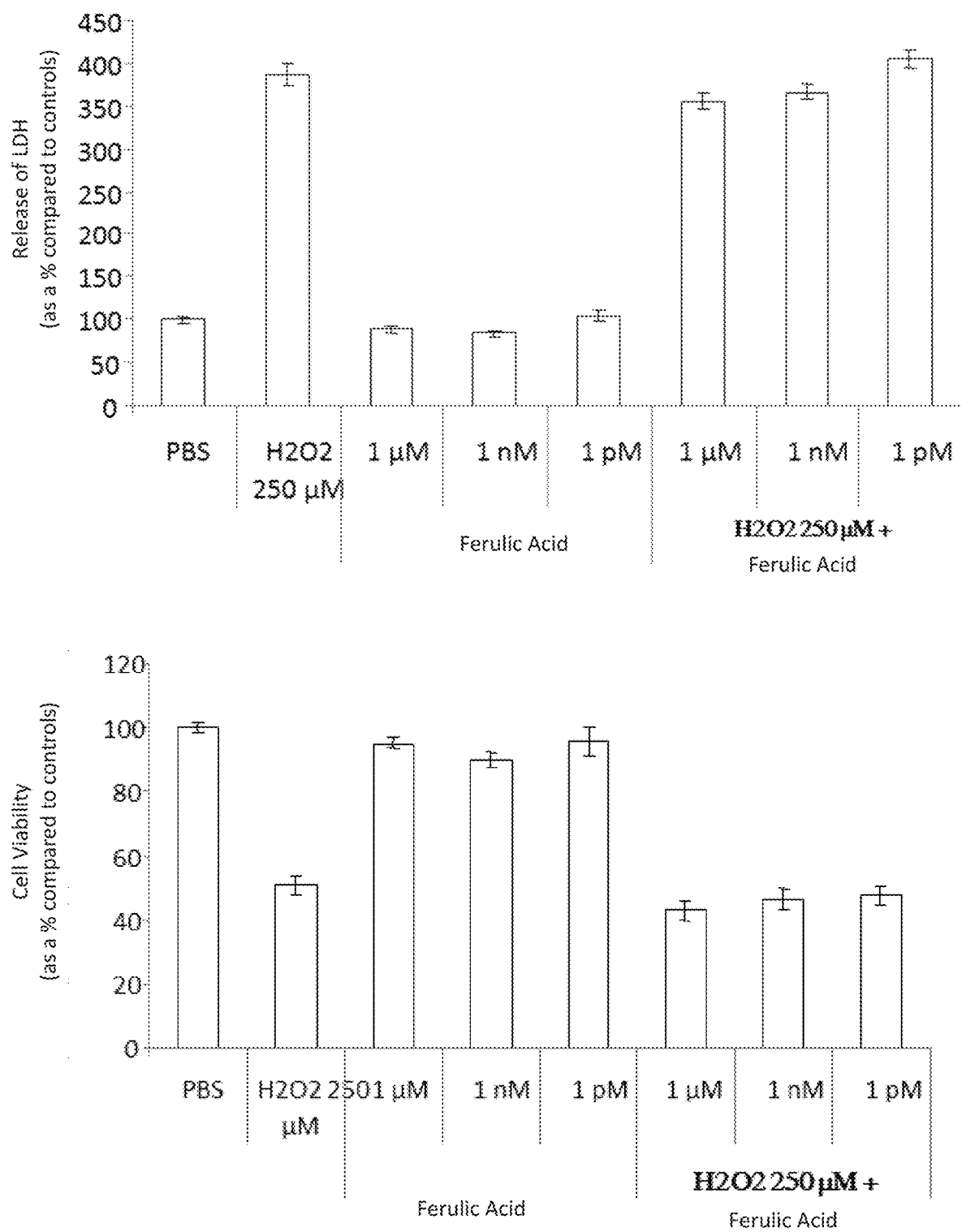
FIG. 4A shows the effects of ferulic acid only on the protection of neuronal cells after an acute treatment.
Figure 4B:
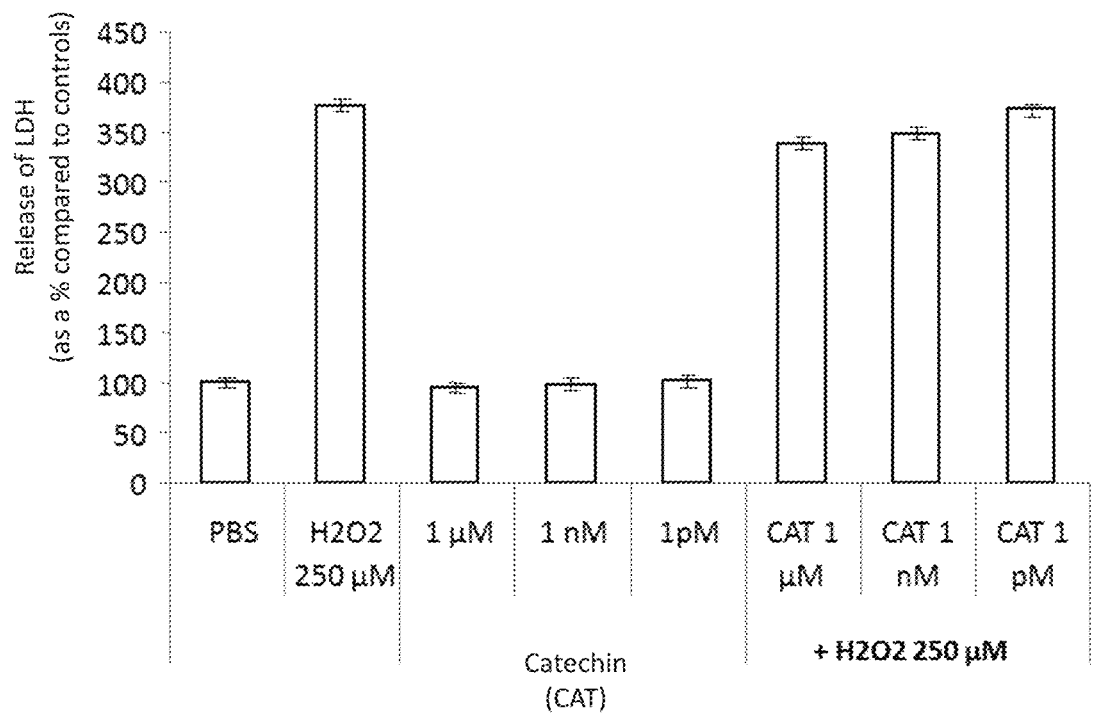
FIG. 4B shows the effects of catechin only on the protection of neuronal cells after an acute treatment.
Figure 4B:
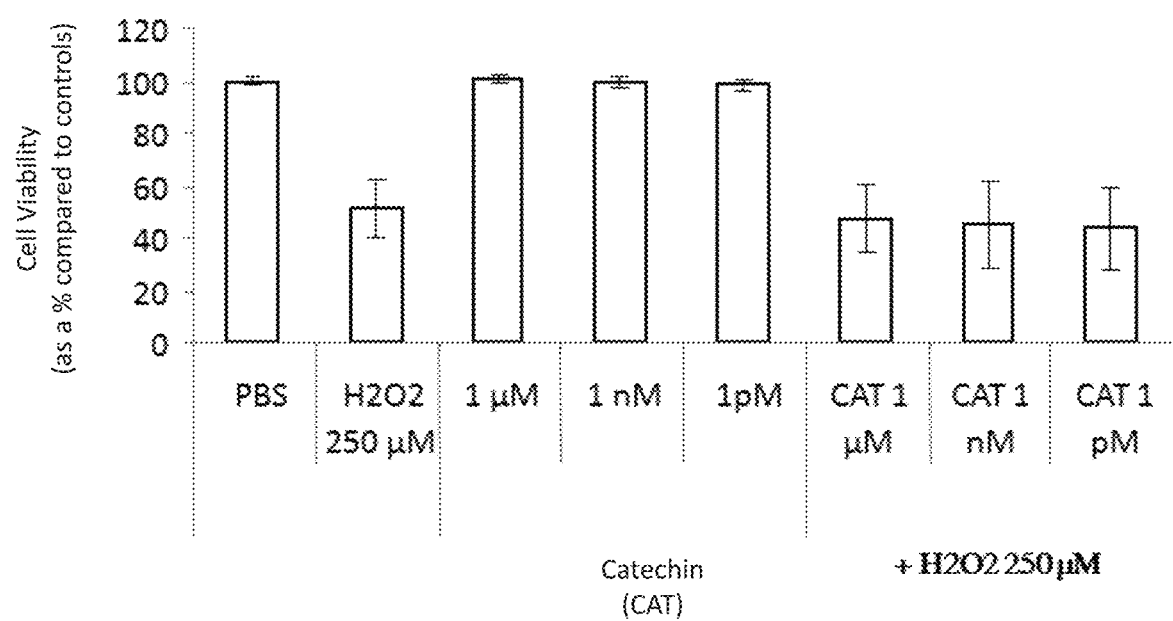
Figure 4C:
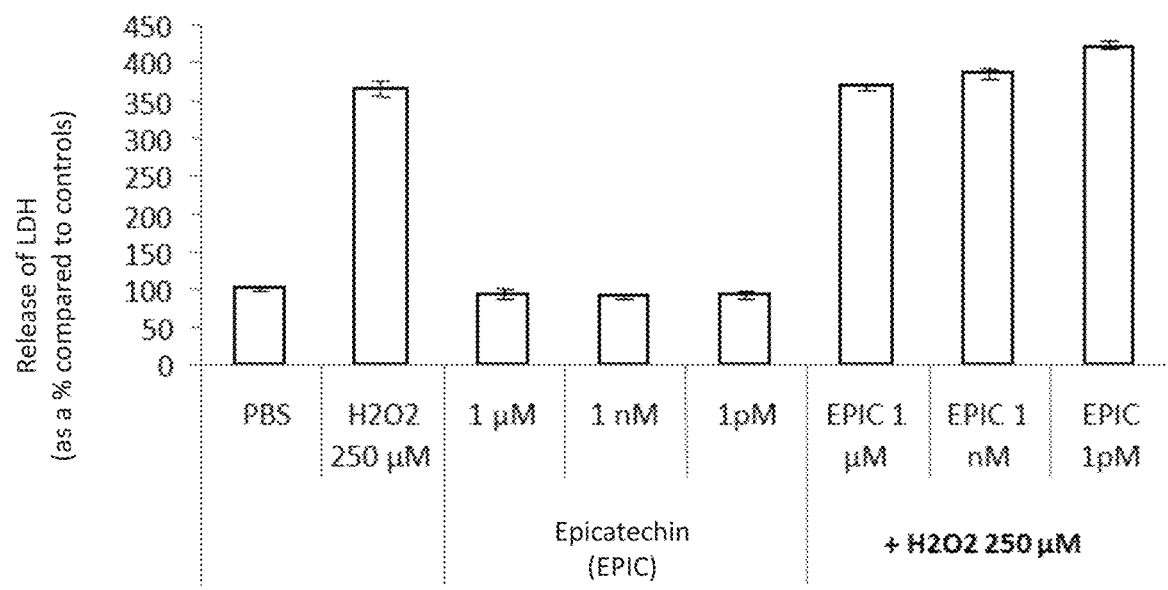
FIG. 4C shows the effects of epicatechin only on the protection of neuronal cells after an acute treatment.
Figure 4C:
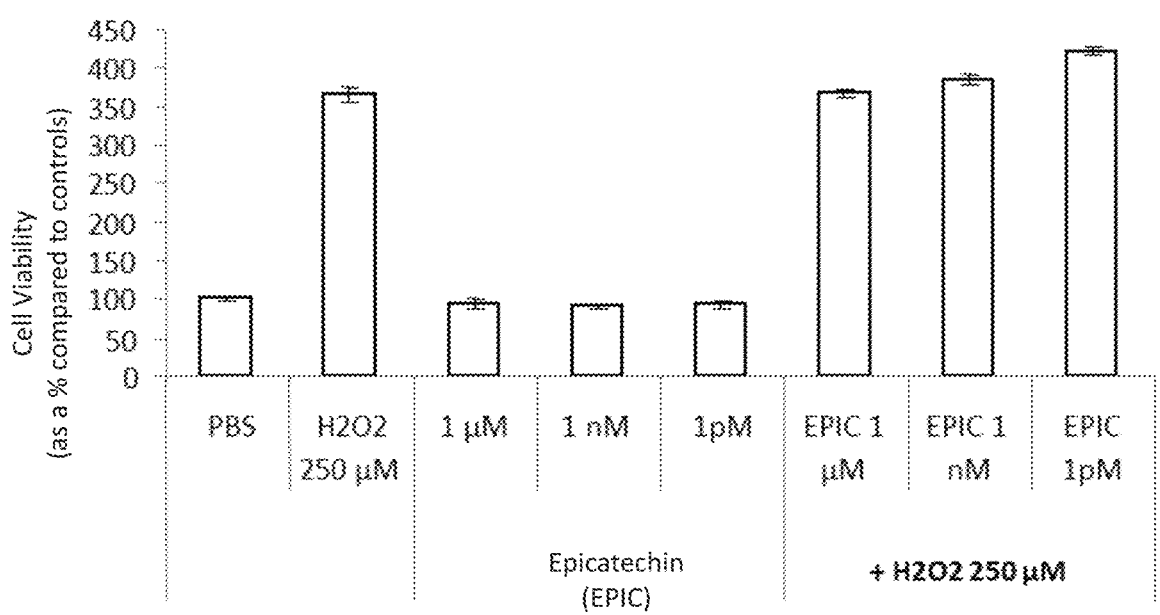
Figure 4D:
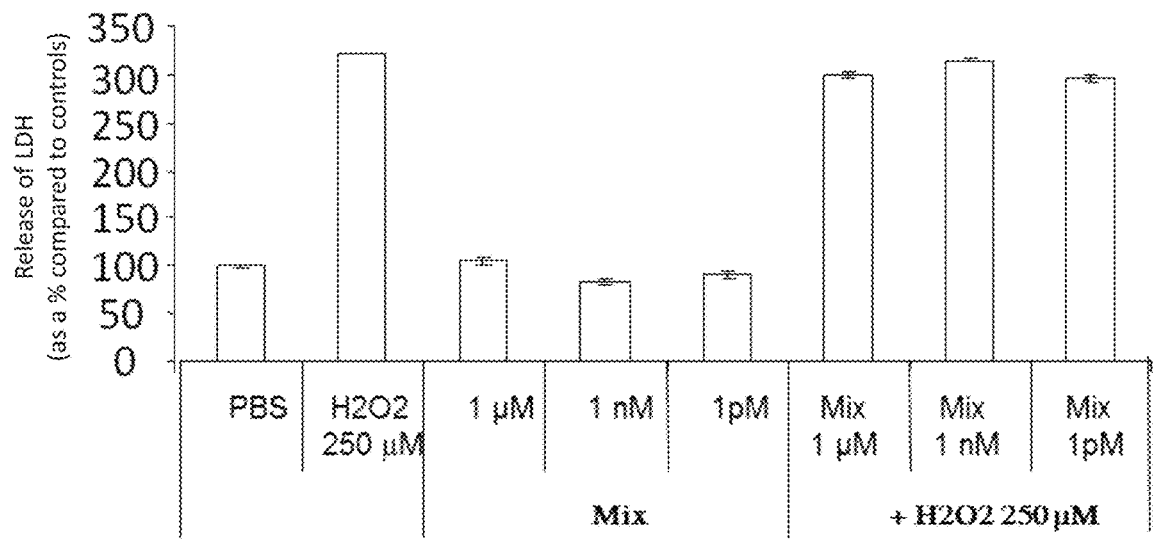
FIG. 4D shows the effects of the agent according to the invention on the protection of neuronal cells after an acute treatment.
Figure 4D:
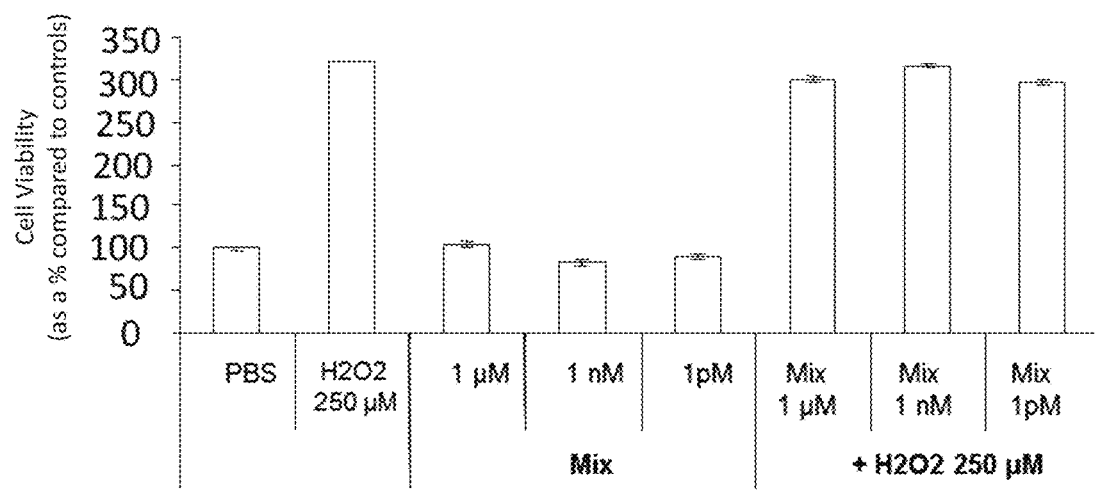

The results are shown in FIGS. 1 to 3.

FIG. 1 shows the differences in bioavailability of the phenolic compounds between an acute and chronic administration of the treatments. The results are given in the form of an average±SEM *** P<0.005 versus acute supplementation. The letters "ns" in the Figure stand for Not Significant.

FIG. 1 shows that no difference is observed in the concentrations of circulating phenolic metabolites between acute supplementation and chronic supplementation for treatments with the extract of *Vitis vinifera* (grape) and with the extract of *Vaccinium angustifolium* (blueberry).

By contrast, the repeated supplementation according to the invention, i.e. extract of *Vitis vinifera* and extract of *Vaccinium angustifolium* for 15 days, is associated with an increase in the concentration of phenolic compounds in plasma (2.1 times more, p=0.0033) compared to mice receiving only one dose.

FIG. 2 shows the ascending hierarchical classification (AHC) of the phenolic metabolites analyzed in the mice before (Day 0) and after (Day 15) chronic ingestion of the three treatments.

Each line corresponds to a detected metabolite and each column to an animal studied. The squares in shades of gray indicate the intensity of the metabolite concentration in the plasma in relation to the average of all of the samples. The boxes represent the phenolic metabolites of the extract of *Vaccinium angustifolium* the concentration of which in the plasma increased significantly with the treatment according to the invention. The data are displayed in the form of an average±SEM **p<0.01 and p*<0.05 vs extract of *Vaccinium angustifolium*, B: extract of *Vaccinium angustifolium*, G: extract of *Vitis vinifera*, N: Agent according to the invention.

The heat map shows that there is no difference in the concentration of circulating phenolic metabolites originating from *Vitis vinifera* between a supplementation with the extract of *Vitis vinifera* (grape) and a supplementation with the agent according to the invention, whereas the phenolic metabolites originating from *Vaccinium angustifolium* were found more extensively in the mouse plasma in the case of supplementation with the agent according to the invention than in the case of supplementation with the extract of *Vaccinium angustifolium* (blueberry). In fact, as can be seen in the boxes, whereas the same quantity of extract of *Vaccinium angustifolium* was administered in both cases, with the agent according to the invention, there was an increase in the absorption of the phenolic compounds of *Vaccinium angustifolium* of 3.0 to 5.5 times. This increase, although smaller (2.3 to 2.8 times) was also observed after acute supplementation with the agent according to the invention versus the extract of *Vaccinium angustifolium*.

FIG. 3 shows the AHC heat map of the phenolic metabolites analyzed in the mouse excrement before (Day 0) and after (Days 1 to 15) chronic ingestion of extract of *Vaccinium angustifolium* (blueberry), extract of *Vitis vinifera* (grape), and the agent according to the invention.

Each line corresponds to the metabolite detected and each column to an animal studied. The squares in shades of gray indicate the intensity of the phenolic metabolite concentration in the excrement in relation to the average of the samples. The boxes represent the phenolic metabolites of *Vaccinium angustifolium* the concentration of which in the excrement decreased significantly when the agent according to the invention was ingested versus the extract of *Vaccinium angustifolium*. The results are given as an average±SEM *** p<0.005 and p*<0.01 versus extract of *Vaccinium angustifolium*, B: extract of *Vaccinium angustifolium*, G: extract of *Vitis vinifera*, N: Agent according to the invention. As observed in the blood samples, no difference was found for the phenolic metabolites of *Vitis vinifera* between supplementation with the agent according to the invention and supplementation with the extract of *Vitis vinifera*, whereas the phenolic metabolites of *Vaccinium angustifolium* were found at significantly lower concentrations in the excrement of mice supplemented with the agent according to the invention in comparison to supplementation with the extract of *Vaccinium angustifolium*. In fact, as can be seen in the boxes, and in line with the previous observations showing an increase in the absorption of the phenolic metabolites of *Vaccinium angustifolium*, in the case of supplementation with the agent according to the invention, it will be observed here too that this supplementation is associated with a reduction in the excretions of the phenolic compounds of *Vaccinium angustifolium* of 2.9 to 6.3 times.

All of these results show that there are synergistic interactions between the extracts of *Vaccinium angustifolium* and *Vitis vinifera* leading to an increase in bioavailability.

Test 2: Bioavailability in Mice Brains

The purpose of this study is to determine whether polyphenols and their metabolic derivatives are capable of accessing the central nervous system, in order to know whether they have effects on the brain.

In order to evaluate the presence of polyphenols in the brain, 6 control mice (3 adults and 3 aged) and 20 supplemented mice (10 adults and 10 aged) were fed with a controlled food free of polyphenols or with a food enriched with the agent according to the invention (Example 1) for 6 weeks. The dose of the agent according to the invention was 500 mg/kg of body weight/day. The mouse brains were recovered at the end of the experiment, dissected and stored at −80° C. The specific polyphenols and metabolites were measured by ultra performance liquid chromatography UPLC-MS/MS.

The results are shown in Table 3 below and in FIGS. 4A to 4D.

TABLE 3

Quantity of polyphenols detected in mice brains

| Content of brain, pmol/g | Control Adult Mice | Control Aged Mice | Agent according to the invention Adult Mice | Agent according to the invention Aged Mice |
| --- | --- | --- | --- | --- |
| Epicatechin | 0 | 0 | 3.54 ± 4.99 | 8.84 ± 15.40 |
| Catechin | 0 | 0 | 0.95 ± 1.45 | 7.12 ± 10.45 |
| PAC-B Dimers | 0 | 0 | 2.70 ± 4.52 | 5.82 ± 8.33 |
| Methyl-catechin glucuronide | 0 | 0 | 5.60 ± 8.56 | 3.15 ± 3.54 |
| Catechin glucuronide | 0 | 0 | 0.81 ± 1.85 | 1.47 ± 1.88 |
| Ferulic Acid | 0 | 0 | 0.80 ± 2.01 | 0.42 ± 0.96 |

After 6 weeks of consuming a food enriched with the agent according to the invention, catechins and epicatechins and their metabolites (methyl-catechin glucuronide, catechin-glucuronide) and ferulic acid were found in the mouse brains. Dimers of proanthocyanidins were also found. These polyphenols were not found in the brains of the control mice. No significant difference was found as regards age. The polyphenols of the agent according to the invention, due to their particular association and their specific quantity can reach the brain directly to produce their neuroprotective effects.

Test 3: Properties of Polyphenols in a Neuronal Cell Culture Model

Like epicatechins, catechin and ferulic acid were detected in the brain. The aim of this study is to test their ability to protect neuronal cells and their potential synergistic effect by using different experimental models.

For this, SK-N-SH cells, a cell line of human neuroblasts, were kept in a MEM supplemented with 10% (v/v) FBS, 100 U/ml of penicillin, 100 µg/ml of streptomycin and 1% sodium pyruvate (1 mM) in a humidified incubator at 37° C. with 5% $CO_2$. The cells were grown to 80% confluence then seeded in multi-well cell culture plates to create different experimental models. The neuroprotective effect of the different compounds was analyzed by two different and complementary tests: the cell death quantification test and the cell survival test.

The cell death test is a colorimetric test based on measuring the activity of the lactate dehydrogenase (LDH) released by the cytosol from damaged cells in the supernatant.

The cell survival test was performed by conducting a Resazurin Test. Resazurin is an oxidation-reduction indicator of the permeable cell that can be used to monitor the number of viable cells by using tetrazolium compounds. The viable cells with an active metabolism can reduce resazurin into a resorufin product that is pink and fluorescent.

Figure 5A:
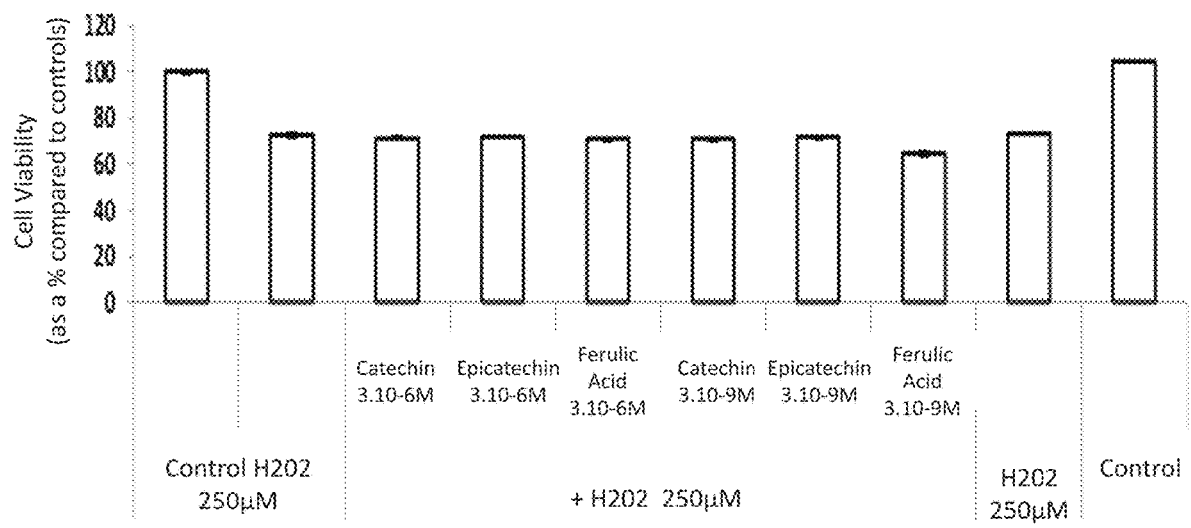
FIG. 5A shows the effects of ferulic acid only, catechin only and epicatechin only on the protection of neuronal cells after three cumulative treatments (cell survival)

SK-N-SH neuronal cells were subjected to a toxic concentration of hydrogen peroxide (250 µM) and co-treated with epicatechin, catechin or ferulic acid at 1 µM, 1 nM and 1 pM for 24 hours. On completing the treatment, the cells were washed twice and cell death (release of LDH) and survival (Resazurin test) were analyzed. The results showing the effects of the three polyphenols taken individually after this acute treatment are shown in FIG. 5A. It will be observed that the polyphenols taken individually do not protect the cells against hydrogen peroxide.

Figure 5B:
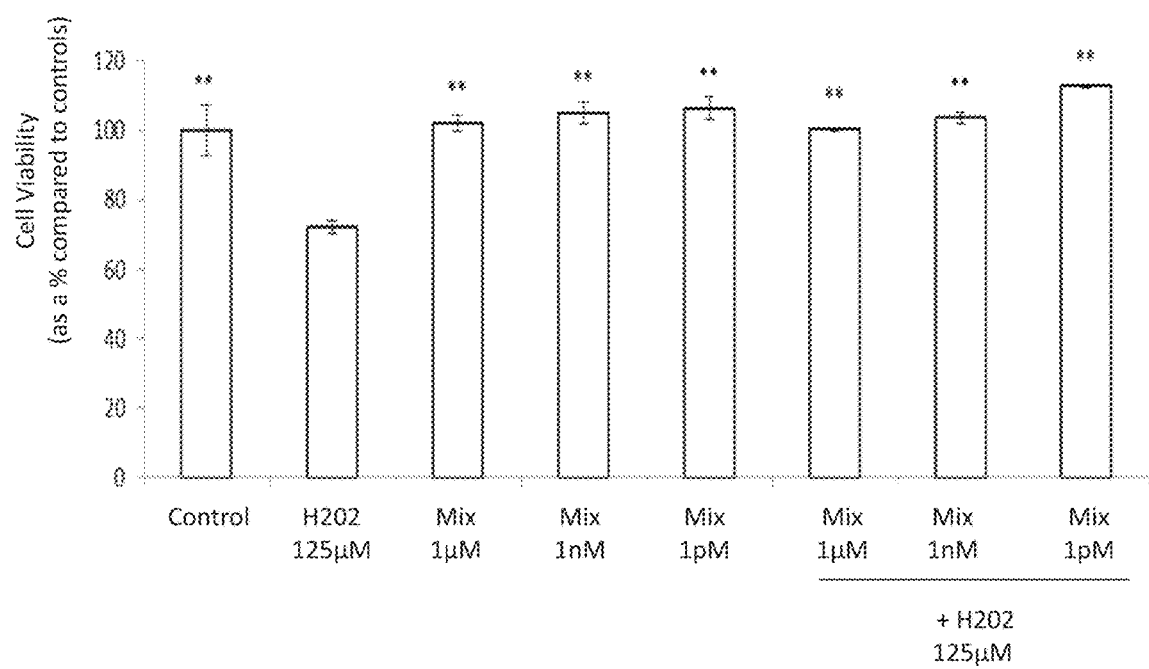
FIGS. 5B, 5C, 5D and 5E show the effects of the agent according to the invention on the protection of neuronal cells after three cumulative treatments at different concentrations (cell survival)

In order to study the synergistic effect of epicatchin, catechin and ferulic acid, the SK-N-SH neuronal cells were subjected for 24 hours to a toxic concentration of hydrogen peroxide and co-treated with a mix comprising epicatechin, catechin and ferulic acid, said mix being tested at the different concentrations of 1 µM, 1 nM or 1 pM. On completing the treatment, the cells were washed twice and the cell death (release of LDH) and survival (Resazurin test) were analyzed. The results showing the effects of three polyphenols combined after this acute treatment are presented in FIG. 5B. It will be observed that the combination of the three polyphenols does not protect the cells against hydrogen peroxide.

Figure 5C:
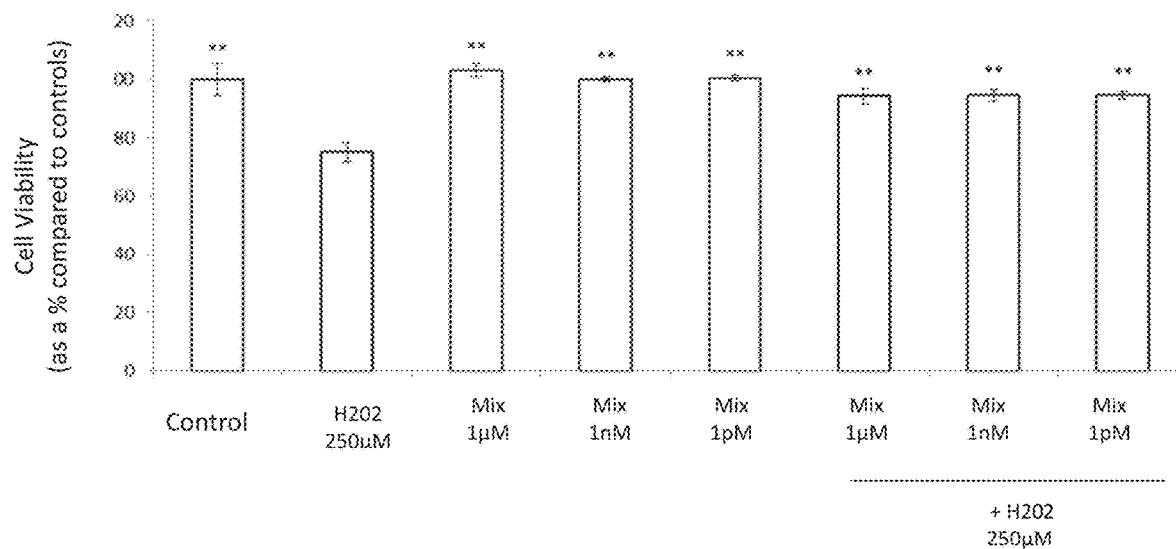

The neuroprotective effects of the three polyphenols, i.e. epicatechin, catechin and ferulic acid, with a cumulative treatment, were then studied. The SK-N-SH cells were grown to 80% confluence then seeded in multi-well cell culture plates. On the following day, each of the three polyphenols were added separately to the 1 µM, 1 nM and 1 pM medium for 3 consecutive days. On the third day, the cells were subjected to a toxic concentration of hydrogen peroxide (250 µM) and the protection was analyzed 24 hours later. On completing the treatment, the cells were washed twice and cell survival (Resazurin test) was analyzed. The results showing the effects of the three polyphenols taken individually (the mix) after this cumulative treatment are shown in FIG. 5C. It will be observed that the polyphenols taken individually do not protect the cells against hydrogen peroxide after 3 days of consecutive treatment.

Figure 5D:
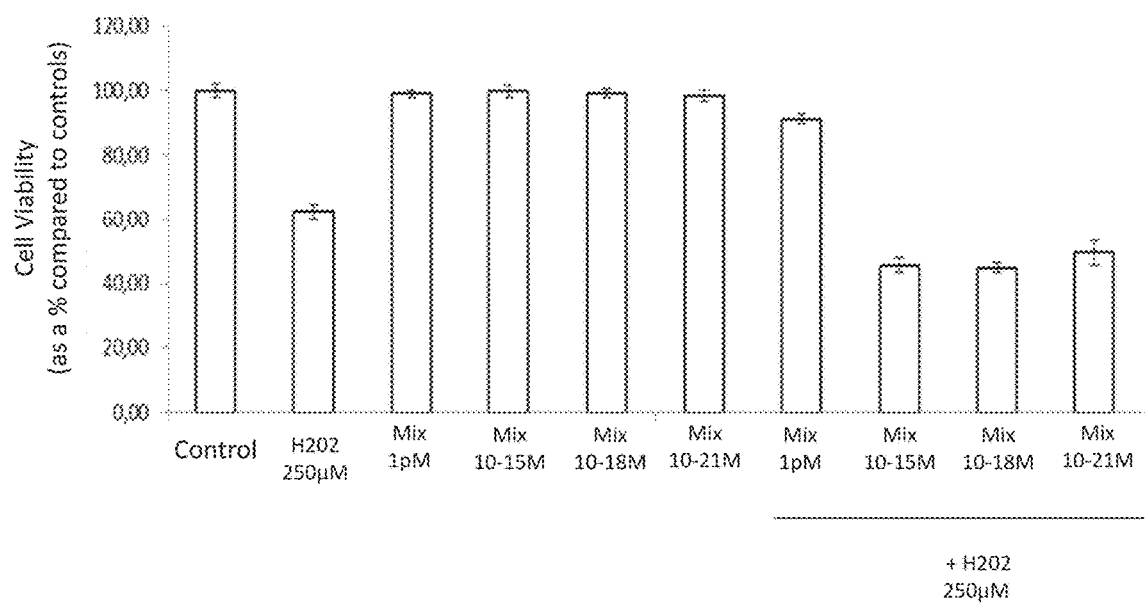
Figure 5E:
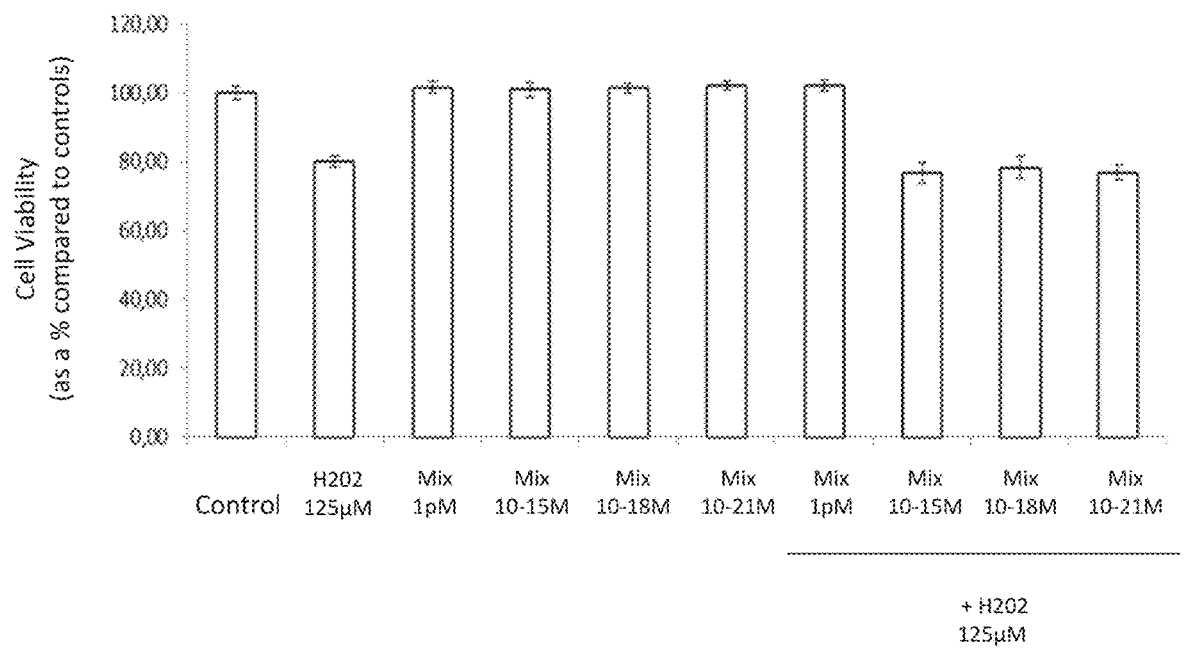
Figure 5F:
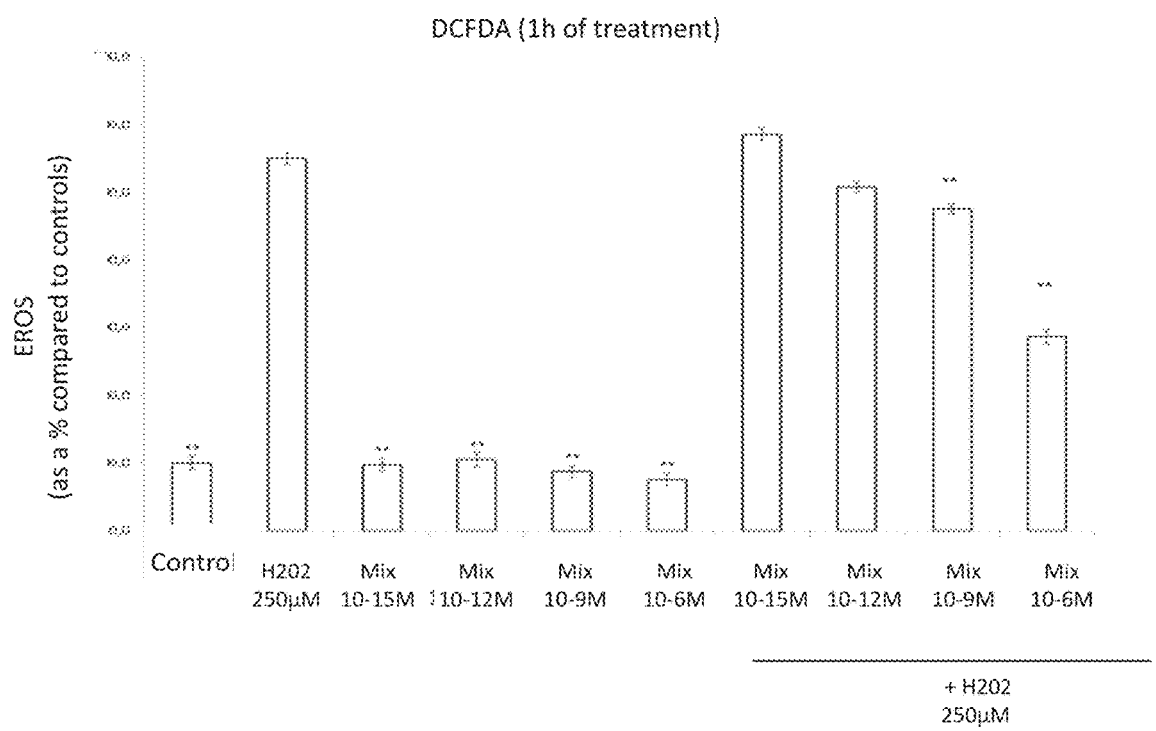
FIG. 5F shows the effects of the agent according to the invention on the protection of neuronal cells after three cumulative treatments (production of ROS)

In order to study the synergistic effect of epicatechin, catechin and ferulic acid, the SK-N-SH cells were grown to 80% confluence then seeded in multi-well cell culture plates. On the following day, a mix of three polyphenols was added to the medium for 3 consecutive days, each polyphenol being present at a concentration of 1 µM, 1 nM or 1 pM in the mix. On the third day, the cells were subjected to a toxic concentration of hydrogen peroxide (125 µM and 250 µM) and the protection was analyzed 24 hours later. On completing the treatment, the cells were washed twice and cell survival (Resazurin test) was analyzed. The results showing the effects of the mix of three polyphenols after this cumuative treatment are shown in FIG. 5D. It will be observed that the mix of epicatechin, catechin and ferulic acid at 1 µM or 1 nM or 1 pM protects the cells against hydrogen peroxide after 3 days of consecutive treatment. The same test was performed with weaker concentrations in the mix of three polyphenols: $10^{-15}$ M, $10^{-18}$ M or $10^{-21}$ M of each polyphenol in the mix. It will be observed in FIG. 5E that with these weaker concentrations, the mix does not protect the cells against toxic hydrogen peroxide concentrations. This clearly shows that the quantity of three specific polyphenols in the agent according to the invention is important to achieve the desired synergistic effect. As the mix of three polyphenols in sufficient quantity is capable of protecting the SK-N-SH neuronal cells after a cumulative treatment, a study of the effect of the mix on the intracellular production of ROS (Reactive Oxygen Species) was then carried out. For this, the cells were grown to 80% confluence then seeded in multi-well cell culture plates. On the following day, a mix containing three polyphenols, i.e. epicatechin, catechin and ferulic acid was added to the medium, each polyphenol being present at a concentration of 1 µM, 1 nM or 1 pM in the mix. On the third day, the SK-N-SH cells were subjected to a toxic concentration of hydrogen peroxide (250 µM) and the level of ROS in the cells was measured using a DCFDA fluorescent probe. The results obtained presented in FIG. 5F show that the mix of three polyphenols containing 1 µM, 1 nM or 1 pM of each of the polyphenols, enables the level of ROS to be reduced in the presence of 250 µM of hydrogen peroxide.

Test 4: Evaluation of the Synergistic Effect in Dogs of the Agent According to the Invention The purpose of this test is to check the efficacy of an agent according to the invention (mix of Example 2) on the antioxidant status of adult dogs by comparing this efficacy to that of an extract of Vitis vinifera, an extract of Vaccinium angustifolium and a control.

Nine beagles (6 males and 3 females, BCS (body condition score) 5/9, average age 20±0.9 months, average weight 9.1±0.4 kg) were fed on a maintenance regime to maintain their body weight. The dogs' food was supplemented with gelatin capsules (Cooper, Melun Cedex, France) containing either:
- a maltodextrin (Control placebo: Glucidex12 Batch #421A323532, Roquette, Lestrem Cedex, France),
- an extract of Vitis vinifera (Grape: Neurogrape Inside PC PR120 BatchAI50288, Activ'Inside, Libourne, France),
- an extract of Vaccinium angustifolium (Wild blueberry extract 0.4 TP Batch #294, Nutra Canada, Quebec, Canada),
- the mix of Example 2 (4 mg/kg of body weight/day).

The experiment was designed as a crossover study where the dogs were fed with experimental rations with the supplementation capsule for 28 days with a one week of wash out between each supplementation period. Each dog thus received each of the four supplementations. Blood samples were taken from the jugular vein before and after each supplementation and were kept in ice. The plasma was recovered by centrifugation at 2124 g of total blood for 10 min at 4° C. Aliquots of plasma were incubated at 80° C.

The oxidant status was evaluated by measuring the total antioxidant status (TAS). For this, a colorimetric-based assay available from RANDOX Laboratories (Ref. NX2332, Crumlin, County Antrim, UK) was used to evaluate the TAS. The method involves incubating 2,2'-Azino-di-[3-ethylbenzthiazoline sulfonate] (ABTS) with a peroxidase (metmyoglobin) and hydrogen peroxide to produce the ABTS$^+$ radical cation. It has a relatively stable blue/green color, measured at 600 nm. The presence of antioxidants in the samples causes suppression of this color production to a degree which is proportional to their concentration. The TAS is expressed in mmol/L.

In order to compare the four regimes with one another, the ΔTAS was determined by comparing the TAS before and after supplementation: ΔTAS=Day 28 TAS−Baseline TAS. The ΔTAS was analyzed by using a mixed-effect model. This model includes the fixed categorical effects of the Baseline, the treatment and the randomization order. It was implemented with SAS (v9.4) software, a mixed procedure with an unstructured correlation matrix to model the within-animal errors. Parameters were estimated using the restricted maximum likelihood method with the Newton-Raphson algorithm. Denominator degrees of freedom were estimated using the Satterthwaite approximation. All the effects were evaluated with an a degree=0.10.

The Wilcoxon test was used to compare changes in the TAS value before and after supplementation.

Figure 6:
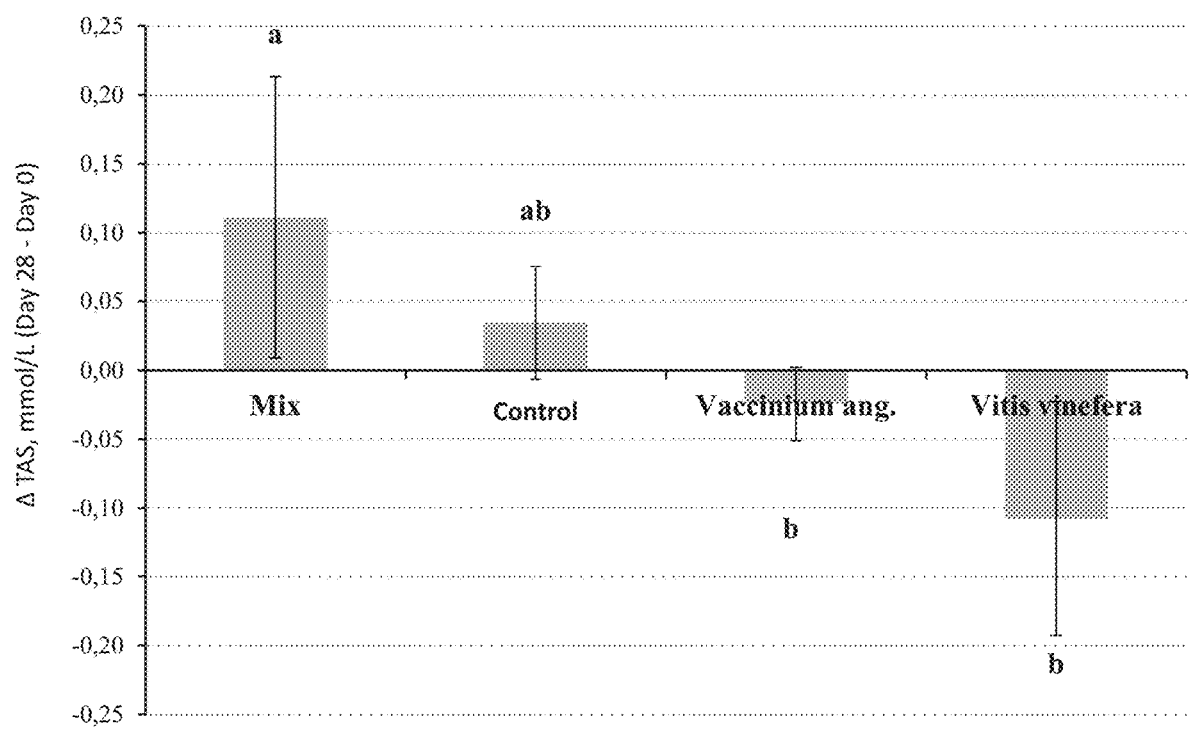
FIG. 6 represents the total antioxidant status (TAS) of adult dogs having been treated with the agent according to the invention, an extract of *Vitis vinifera*, an extract of *Vaccinium angustifolium*, and a control.

The results obtained are presented in Table 4 (mean, standard error and Wilcoxon test) and in FIG. 6.

TABLE 4

TAS (mmol/L) (Mean ± SEM) for groups of adult dogs (n = 9) fed on different supplementation regimes: agent according to the invention (Invention) extract of Vitis vinifera (Vv), extract of Vaccinium angustifolium (Va) or maltodextrin (Control) for 28 days.

| | | Day 0 | | Day 28 | | p-value |
|---|---|---|---|---|---|---|
| | | Mean | Standard Error | Mean | Standard Error | (Wilcoxon) Treatment |
| TAS mmol/L | Va | 0.92 | 0.122 | 0.90 | 0.109 | NS |
| | Invention | 0.81 | 0.052 | 0.93 | 0.070 | 0.023 |
| | Vv | 0.97 | 0.155 | 0.87 | 0.077 | NS |
| | Control | 0.84 | 0.048 | 0.88 | 0.075 | NS |

It will be observed in the Table and FIG. 6 that the mix according to the invention increases significantly and synergistically the TAS concentration compared to the extract of Vitis vinifera or the extract of Vaccinium angustifolium on their own.

Moreover, the results of the Wilcoxon test show that the invention is the only supplementation that presents significantly higher TAS concentrations after supplementation. Supplementation with extracts of Vitis vinifera or extract of Vaccinium angustifolium on their own do not significantly change the TAS concentration.

Thus, supplementation with a mix of molecules from Vitis vinifera and from Vaccinium angustifolium according to the invention has a synergistic effect on the total antioxidant status of animals compared to supplementations with an extract of Vitis vinifera and an extract of Vaccinium angustifolium taken alone.

Test 5: Evaluation of the Effect on the Memory

The purpose of this study is to check the effect of a double dose of mix according to the invention (Example 2) on the memory levels of dogs.

The study is a blind randomized preclinical study in which a longitudinal parallel group model was used. Thirty-five beagles (Vivocore Inc. Company, Toronto, Canada; 14 males and 21 females; aged between 8.0 and 14.5 years at the beginning of the study) were allocated in three groups for the experiment, three weeks before the start of the supplementations. The allocation of the dogs was determined by performance levels (cumulative scores) based on DNMP (Delayed Non-Matching Position) test scores, so that each group had a substantially equivalent total DNMP test score.

The three groups of dogs were then fed respectively with kibbles containing in inclusion either 0 ppm (placebo), or 240 ppm of the mix of Example 2, or 480 ppm of the mix of Example 2 (ppm relative to the kibble weight).

The DNMP test was performed from Day −27 to −16 and the analysis was performed from Day 58 to 63.

The DNMP test comprises two phases:
Phase 1: the dog must move an object placed in one of three possible positions on a food well. The block to be removed covers a reward.
Phase 2: after a 20 s to 90 s attempt, two objects identical to the first phase are presented to the dog. One object is located in the same position as in the first phase. However, the correct object is placed in one of the two remaining positions (non match), and if the dog moves this object, he receives the reward.

For the present study, 12 DNPM test sessions were carried out, with one test session per day for all of the subjects. The variable-delay subtask was used. For each test session, delays of 20 and 90 seconds were equally distributed over the 12 tests, enabling evaluation of working memory. An inter-test interval of 30 seconds was applied. There were 6 sessions for the initial phase and six sessions for the treatment phase. The subjects were tested on each of the designated days, regardless of the score.

Throughout all the test procedures, the animals were rewarded with Purina Essential Care Adult Formula tinned wet dog food.

In order to compare the three treatments to the DNMP results, the increase in relation to the Baseline was analyzed using a Chi-squared test. The analysis was performed using SAS (v9.4) software with a significant level of $\alpha=0.05$.

Figure 7:
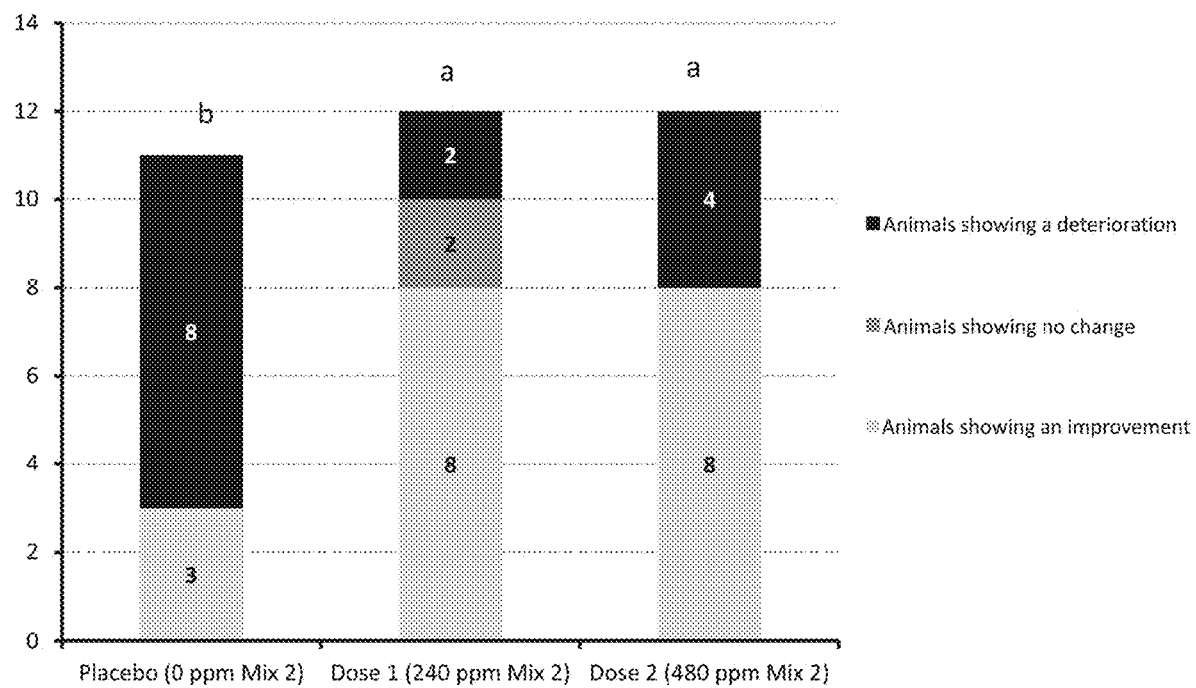
FIG. 7 shows the effect on the cognitive functions of dogs of an agent according to the invention at different doses, in comparison to a placebo.

The results are presented in FIG. 7. A significant cognitive increase was observed when the dogs received a treatment according to the invention (Mix 2) compared to dogs that did not receive the treatment. Moreover, the quantity of treatment did not affect the number of dogs showing a significant increase, which proves that, in dogs, the effectiveness is independent of the treatment dose.

Test 6: Evaluation of the Effect on a Dog's Tolerance

The purpose of this test is to check the food safety of the nutritional or therapeutic food agent of the invention on dogs, by checking certain renal biomarkers. Indeed, numerous publications have reported a toxicity of grapes in dogs, causing them renal deficiencies the symptoms of which are manifested as vomiting, diarrhea, etc. (Eubig P, Brady M, Gwaltney-Brant S, Khan S, Mazzaferro E, Morrow C (2005). "*Acute renal failure in dogs after the ingestion of grapes or raisins: a retrospective evaluation of 43 dogs*" (1992-2002).

Twenty-four beagles (20 males and 4 females, BCS 5/9, average age 31±3 months, average weight 11.4±0.2 kg), were fed on a maintenance food regime (Royal Canin Medium Adult, France) in order to maintain their optimal weight during the test. Four groups of 6 dogs thus each received supplements, i.e. capsules containing maltodextrin (placebo) or an agent according to the invention, i.e. the mix as prepared in Example 2: 4 (Mix 1), 20 (Mix 5), and 40 (Mix 10) mg/kg of body weight/day.

Urine and blood samples were taken at the start of the test (Week 0), after 12 weeks and after 24 weeks.

The Cystatin C (CysC), clusterin and neutrophil gelatinase-associated lipocalin (NGAL) of the plasma and urine were analyzed in the blood samples (Tvarijonaviciute A, Ceron J J, Holden S L, Biourge V, Morris P J, German A J. Effect of Weight Loss in Obese Dogs on Indicators of Renal Function or Disease. J. Vet. Intern. Med. 2013; 27:31-38; Garcia-Martinez J D, Tvarijonaviciute A, Ceron J J, Calden M, Martinez-Subierla S. Urinary Clusterin as a Renal Marker in Dogs. J. Vet. Diagn. Invest. 2012; 24:301-306). Each parameter was analyzed by means of a mixed-effect model, by evaluating the effects of the baseline, day, treatment and the day x of treatment (SAS v9.4; $\alpha=0.05$).

As shown in Table 5, the biomarkers were found in quantities below the upper limit obtained with the control and experimental treatments at Week 0 (plasma CysC, urinary CysC/Crea ratio, urinary clusterin/Creat ratio, NGAL plasma and urinary/Creat NGAL at 2.23 µg/mL, 156 ng/g, 443 ng/g, 47 ng/mL, 28.5 ng/g respectively).

TABLE 5

|  |  | CysC, µg/mL | | Urinary CysC/Creat ratio, µg/g | | Urinary Clusterin/Creat ratio, ng/g | | NGAL, ng/mL | | Urinary NGAL/Creat ratio, ng/g | |
| --- | --- | --- | --- | --- | --- | --- | --- | --- | --- | --- | --- |
|  |  | Mean | SEM | Mean | SEM | Mean | SEM | Mean | SEM | Mean | SEM |
| Week 0 | Control | 1.25 | 0.085 | 18.90 | 17.243 | 79.3 | 20.05 | 17.8 | 4.52 | 11.12 | 4.688 |
|  | Mix 1 | 1.25 | 0.152 | 30.38 | 25.390 | 44.5 | 13.22 | 17.0 | 5.02 | 7.97 | 4.487 |
|  | Mix 5 | 1.17 | 0.084 | 27.37 | 14.261 | 63.4 | 27.53 | 14.9 | 3.49 | 4.18 | 1.786 |
|  | Mix 10 | 1.47 | 0.161 | 12.20 | 4.441 | 83.7 | 22.67 | 18.0 | 3.00 | 5.45 | 1.019 |
| Week 12 | Control | 1.18 | 0.075 | 8.25 | 3.156 | 61.1 | 34.07 | 23.8 | 5.21 | 8.42 | 3.690 |
|  | Mix 1 | 1.27 | 0.173 | 9.83 | 4.594 | 67.9 | 33.33 | 15.3 | 4.69 | 5.68 | 1.934 |
|  | Mix 5 | 1.22 | 0.079 | 5.12 | 1.696 | 39.5 | 17.16 | 12.9 | 2.80 | 4.00 | 1.551 |
|  | Mix 10 | 1.35 | 0.099 | 12.93 | 6.086 | 98.7 | 52.59 | 19.7 | 4.03 | 4.72 | 1.552 |
| Week 24 | Control | 1.10 | 0.132 | 14.27 | 9.840 | 135.1 | 66.10 | 23.7 | 2.67 | 7.33 | 2.483 |
|  | Mix 1 | 1.23 | 0.182 | 4.13 | 1.406 | 94.2 | 69.26 | 19.3 | 4.80 | 4.92 | 1.352 |
|  | Mix 5 | 1.18 | 0.079 | 21.42 | 11.941 | 56.2 | 24.72 | 14.3 | 4.04 | 3.52 | 0.297 |
|  | Mix 10 | 1.30 | 0.116 | 3.80 | 1.240 | 47.5 | 20.23 | 20.7 | 3.53 | 4.55 | 1.393 |
| p-values | treatment | NS | | NS | | NS | | NS | | NS | |
|  | day | NS | | NS | | NS | | NS | | NS | |
|  | Treatment x day | NS | | NS | | NS | | NS | | NS | |

Adult dogs consuming the agent according to the invention therefore show no clinical signs of intolerance, even at the maximum dose tested (10 times the normal dose).

Test 7: Effect on Alzheimer's Disease

This test was performed on a heterozygote 3×Tg-AD mouse model as described for example in Arsenault D, Dal-Pan A, Tremblay C, Benett D A, Guitton M J, et al. (2013) *P4K Inactivation Impairs Social Recognition in 3×Tg-AD Mice without increasing Brain Deposition of Tau and Aβ*. The Journal of Neuroscience 33: 10729-10740.

120 non-transgenic (Non Tg) and triple transgenic (3×Tg-AD) mice aged 12 months were used for this test. Seven mice died before the test and were excluded.

In addition, an additional group of 4-month-old C57BL/6 mice was used as a control group. The agent according to the invention of Example 1 was introduced into mouse food pellets. The mice were fed for 4 months with a control food or with 500 mg of extract/kg of body weight/day (reference "Polyph1") or 2500 mg of extracts/k of body weight/day (reference "Polyph2").

Three months after the start of the test, behavioral analyses were conducted. After an additional month, the mice were placed under deep anesthesia and extracts of intracardiac blood were taken. They were then perfused with an intracardiac perfusion with a saline phosphate buffer containing protease inhibitors and phosphatase inhibitors. Extracts of parietal-temporal cortex were then dissected, frozen and kept at −80° C. They were then treated for ELISA, Western Blot and immunofluorescence analysis to measure the following markers: beta-amyloid (Aβ), Tau protein and BDNF (Brain-Derived Neurotrophic Factor). First of all, a cognitive decline was observed in 3×Tg-AD and non-Tg 15-month-old mice compared to non-Tg 4-month-old mice (control). In fact, for the aged mice a reduction was observed in the recognition ratio or recognition index during the novel object recognition test. Advantageously, the administration of the agent according to the invention at doses of 500 or 2500 mg/kg/day prevents the deterioration of the memory in 3×Tg-AD mice.

Furthermore, the agent according to the invention prevents the reduction of BDNF (Brain-Derived Neurotrophic Factor) in 16-month-old 3×Tg-AD mice.

Lastly, the results obtained show that phenolic metabolite concentrations are correlated with the cognitive performance (memory) of mice supplemented with the agent according to the invention.

The invention claimed is:

1. A nutritional or therapeutic agent consisting essentially of a mix obtained from *Vitis vinifera* and *Vaccinium angustifolium* extracts, wherein the mix contains:
   at least 1% of catechins and/or epicatechins, the percentage being given by weight in relation to the total weight of the mix,
   at least 5 ppm (parts per million in the mix) of ferulic acid; and
   at least 200 ppm of resveratrol;
   malvidin 3-glucoside at a concentration of at least 300 ppm,
   at least 50 ppm of quercetin and/or quercetin glycosides, and
   at least 500 ppm of anthocyanidins; and
   wherein the nutritional or therapeutic agent formulated as a tablet, capsule, gel capsule, microcapsule, suspension, emulsion, food supplement, drink or food for humans or animals.

2. The agent according to claim 1, characterized in that the mix comprises at least 5% of catechins and/or epicatechins, the percentage being given by weight in relation to the total weight of the mix.

3. The agent according to claim 1, characterized in that the mix comprises at least 10 ppm (parts per million in the mix) of ferulic acid.

4. The agent according to claim 1, characterized in that the extract of *Vitis vinifera* has a flavanol polymer content of less than 0.5% by weight of the total weight of the polyphenols of the extract.

5. The agent according to claim 1, for use as a drug for humans or animals.

6. The agent according to claim 1, for use in the treatment or prevention in humans or animals of Alzheimer's disease and/or Parkinson's disease and/or Huntington's disease and/or pathological cognitive decline and/or dementia and/or depression and/or diabetes and/or schizophrenia and/or mental retardation and/or disorders relating to the postmenopausal condition in women and/or cognitive dysfunction syndrome (CDS).

7. The agent for a use according to claim 5, at a dose allowing humans or animals to be provided with:
   at least 100 µg per kg of body weight of catechins and/or epicatechins,
   at least 0.05 µg per kg of body weight of ferulic acid, and
   at least 10 µg per kg of body weight of resveratrol.

8. The agent for a use according to claim 5, at a dose allowing humans or animals to be provided with:
   at least 0.2 µg per kg of body weight of quercetin and/or quercetin glycosides, and
   at least 1 µg per kg of body weight of anthocyanidins.

9. A method of improving cognitive functions and/or executive functions, and/or limiting age-related non-pathological cognitive decline comprising administering the agent according to claim 1 to healthy humans or animals.

10. The method according to claim 9, wherein there is an improvement to one or more of the group selected from memory, attention, concentration, alertness, learning, intelligence, language, mood, stress, anxiety, outlook, and sleep.

11. The method according to claim 9, wherein said agent is administered in a quantity providing the humans or animals with:
   at least 100 µg per kg of body weight of catechins and/or epicatechins,
   at least 0.05 µg per kg of body weight of ferulic acid, and
   at least 10 µg per kg of body weight of resveratrol.

12. The method according to claim 9, wherein said agent is administered in a quantity providing the humans or animals with:
   at least 0.2 µg per kg of body weight of quercetin and/or quercetin glycosides,
   and
   at least 1 µg per kg of body weight of anthocyanidins.

* * * * *